(12) United States Patent
Bawendi et al.

(10) Patent No.: US 7,060,243 B2
(45) Date of Patent: *Jun. 13, 2006

(54) TELLURIUM-CONTAINING NANOCRYSTALLINE MATERIALS

(75) Inventors: Moungi G. Bawendi, Boston, MA (US); Frederic V. Mikulec, Austin, TX (US); Sungjee Kim, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 227 days.

This patent is subject to a terminal disclaimer.

(21) Appl. No.: 10/456,592

(22) Filed: Jun. 9, 2003

(65) Prior Publication Data

US 2005/0031888 A1    Feb. 10, 2005

Related U.S. Application Data

(60) Division of application No. 09/625,861, filed on Jul. 26, 2000, now Pat. No. 6,607,829, and a continuation-in-part of application No. 08/969,302, filed on Nov. 13, 1997, now Pat. No. 6,322,901.

(60) Provisional application No. 60/145,708, filed on Jul. 26, 1999.

(51) Int. Cl.
*C01B 19/00* (2006.01)

(52) U.S. Cl. ............ 423/508; 423/99; 423/155

(58) Field of Classification Search ............... 427/215, 427/217, 220, 229; 423/508, 99, 155
See application file for complete search history.

(56) References Cited

U.S. PATENT DOCUMENTS

| | | | |
|---|---|---|---|
| 3,996,345 A | 12/1976 | Ullman et al. ............. 424/12 |
| 4,637,988 A | 1/1987 | Hinshaw et al. ............ 436/546 |
| 4,777,128 A | 10/1988 | Lippa ........................... 435/5 |
| 5,262,357 A | 11/1993 | Alivisatos et al. .......... 437/233 |
| 5,293,050 A | 3/1994 | Chapple-Sokol et al. ..... 257/17 |
| 5,304,786 A | 4/1994 | Pavlidis et al. ............ 235/462 |
| 5,354,707 A | 10/1994 | Chapple-Sokol et al. ... 437/106 |
| 5,395,791 A | 3/1995 | Cheng et al. |
| 5,422,489 A | 6/1995 | Bhargava ................ 250/488.1 |
| 5,492,080 A | 2/1996 | Ohkawa et al. |
| 5,499,260 A | 3/1996 | Takahashi et al. |
| 5,505,928 A | 4/1996 | Alivisatos et al. .......... 423/299 |
| 5,515,393 A | 5/1996 | Okuyama et al. |
| 5,525,377 A | 6/1996 | Gallagher et al. .......... 427/512 |
| 5,537,000 A | 7/1996 | Alivisatos et al. .......... 313/506 |
| 5,541,948 A | 7/1996 | Krupke et al. ................ 372/51 |
| 5,565,324 A | 10/1996 | Still et al. ....................... 435/6 |
| 5,585,640 A | 12/1996 | Huston et al. ............ 250/483.1 |
| 5,625,456 A | 4/1997 | Lawandy .................... 356/376 |
| 5,674,698 A | 10/1997 | Zarling et al. ............. 435/7.92 |

(Continued)

FOREIGN PATENT DOCUMENTS

WO    WO 95/29473    11/1995

(Continued)

OTHER PUBLICATIONS

Murray, "Colloidal synthesis of nanocrystals and nanocrystal superlattices", IBM Journal of Research and Development, Jan. 2001.*

(Continued)

*Primary Examiner*—H. Thi Le
(74) *Attorney, Agent, or Firm*—Steptoe & Johnson LLP

(57) ABSTRACT

Tellurium-containing nanocrystallites are produced by injection of a precursor into a hot coordinating solvent, followed by controlled growth and annealing. Nanocrystallites may include CdTe, ZnTe, MgTe, HgTe, or alloys thereof. The nanocrystallites can photoluminesce with quantum efficiencies as high as 70%.

14 Claims, 17 Drawing Sheets

U.S. PATENT DOCUMENTS

| | | | |
|---|---|---|---|
| 5,721,099 A | 2/1998 | Still et al. ................. | 435/6 |
| 5,736,330 A | 4/1998 | Fulton ...................... | 435/6 |
| 5,747,180 A | 5/1998 | Miller et al. | |
| 5,751,018 A | 5/1998 | Alivisatos et al. ......... | 257/64 |
| 5,770,299 A | 6/1998 | Dannenhauer et al. ..... | 428/195 |
| 5,789,162 A | 8/1998 | Dower et al. ............... | 435/6 |
| 5,882,779 A | 3/1999 | Lawandy | |
| 5,985,353 A | 11/1999 | Lawton et al. ............. | 427/2.13 |
| 5,990,479 A | 11/1999 | Weiss et al. ............... | 250/307 |
| 6,251,303 B1* | 6/2001 | Bawendi et al. ........... | 252/301.4 R |
| 6,306,610 B1 | 10/2001 | Bawendi et al. | |
| 6,322,901 B1* | 11/2001 | Bawendi et al. ........... | 428/548 |
| 6,423,551 B1 | 7/2002 | Weiss et al. | |
| 6,576,291 B1* | 6/2003 | Bawendi et al. ........... | 427/215 |
| 6,607,829 B1* | 8/2003 | Bawendi et al. ........... | 428/403 |
| 6,821,337 B1* | 11/2004 | Bawendi et al. ........... | 117/3 |
| 6,921,496 B1* | 7/2005 | Anderson et al. .......... | 252/301.6 S |

FOREIGN PATENT DOCUMENTS

| | | |
|---|---|---|
| WO | WO 97/10175 | 3/1997 |
| WO | WO 98/04740 | 2/1998 |
| WO | 98/19963 | 5/1998 |
| WO | WO 98/33070 | 7/1998 |
| WO | WO 98/36376 | 8/1998 |
| WO | WO 98/46372 | 10/1998 |
| WO | WO 99/26299 | 5/1999 |

OTHER PUBLICATIONS

Alivisatos, "Semiconductor Clusters, Nanocrystals, and Quantum Dots," *Science*, 271:933-937, Feb. 16, 1996.

Alivisatos et al., "Organization of 'nanocrystal molecules' using DNA", *Nature*, 382:609-611, Aug. 15, 1996.

Baldwin et al., "Synthesis of a Small Molecule Combinatorial Library Encoded with Molecular Tags," *J. Am. Chem. Soc.*, 117:5588-5589, 1995.

Bawendi et al., "Luminescence properties of CdSe quantum crystallites: resonance between interior and surface localized states," *J. Chem. Phys.*, 96(2):946-954, Jan. 15, 1992.

Beverloo et al., "Preparation and Microscopic Visualization of Multicolor Luminescent Immunophosphors," *Cytometry*, 13:561-570, 1992.

Chee et al., "Accessing Genetic Information with High-Density DNA Arrays" *Science*, 274(5287):610-614, Oct. 25, 1996.

Coffer et al., "Characterization of quantum-confined CdS Nanocrystallites stabilized by deoxyribonucleic acid (DNA)" *Nanotechnology*, 3:69-76, 1992.

Colvin et al., "Light-emitting diodes made from cadmium selenide nanocrystals and a semiconducting polymer" *Nature*, 370(6488):354-357, Aug. 4, 1994.

Cook, "Scintillation proximity assay: a versatile high-throughput screening technology," *Drug Discovery Today*, 1(7):287-294, Jul. 1996.

Czarnik, "Encoding methods for combinatorial chemistry" *Curr Opin Chem Biol.*, 1(1):60-66, 1997.

Danek et al., "Synthesis of Luminescent Thin-Film CdSe/ZnSe Quantum Dot Composites Using CdSe Quantum Dots Passivated with an Overlayer of ZnSe" *Chem. Mater.*, 8(1):173-180, 1996.

Egner et al., "Tagging in combinatorial chemistry: the use of coloured and fluorescent bads" *Chem. Commun.*, 735-736, Apr. 21, 1997.

Fodor, "Techwire" *Science*, 277(5324):393-395, Jul. 18, 1997.

Guha et al., "Hybrid organic-inorganic semiconductor-based light-emitting diodes" *J. Appl. Phys.*, 82(8):4126-4128, Oct. 15, 1997.

Jarvis et al., "Solution Synthesis and Photoluminescence Studies of Small Crystallites of Cadmium Telluride," *Mat. Res. Soc. Symp. Proc.*, 272:229-234, 1992.

Kagan et al., "Electronic Energy Transfer in CdSe Quantum Dot Solids," *Physical Review Letters*, 76(9):1517-1520, Feb. 26, 1996.

Kagan et al., "Long-range resonance transfer of electronic excitations in close-packed CdSe quantum-dot solids," *Physical Review B*, 54(12):8633-8643, Sep. 15, 1996-II.

Lee et al., "Surface Derivatization of Nanocrystalline CdSe Semiconductors," *Mat. Res. Soc. Symp. Proc.*, 452:323-328, Mar. 13, 1997.

Liz-Marzan et al., "Synthesis of Nanosized Gold-Silica Core-Shell Particles" *Langmuir*, 12(18):4329-4335, 1996.

Mahtab et al., "Protein-Sized Quantum Dot Luminescence Can Distinguish between 'Straight', 'Bent', and 'Kinked' Oligonucletides", *J. Am. Chem. Soc.*, 117:9099-9100, 1995.

Mahtab et al., "Preferential-Absorption of a 'Kinked' DNA to a Neutral Curved Surface: Comparison to and Implications for Nonspecific DNA-Pprotein Interactions," *J. Am. Chem. Soc.*, 118(30):7028-7032, 1996.

McGall et al., "Light-directed synthesis of high-density oligonucleotide arrays using semiconductor photoresists" *Proc. Natl. Acad. Sci. USA*, 93:13555-13560, Nov. 1996.

Moran et al., "Radio Frequency Tag Encoded Combinatorial Library Method for the Discovery of Tripeptide-Substituted Cinnamic Acid Inhibitors of the Protein Tyrosine Phosphatase PTP1B" *J. Am. Chem. Soc.*, 117:10787-10788, 1995.

Müllenborn et al., "Characterization of Solution-Synthesized CdTe and HgTe," *Applied Physics*, 56:317-321, 1993.

Murphy et al., "Quantum Dots as Inorganic DNA-Binding Proteins," *Mat. Res. Soc. Symp.*, 452:597-600, Mar. 13, 1997.

Nicolaou et al., "Radiofrequency Encoded Combinatorial Chemistry" *Ingew. Chem. Int. Ed. Engl.*, 34(20):2289-2291, 1995.

Pehnt et al., "Nanoparticle precursor route to low-temperature spray deposition of CdTe thin films," *Appl. Phys. Lett.*, 67(15):2176-2178, Oct. 1995.

Peng et al., "Epitaxial Growth of Highly Luminescent CdSe/CdS Core/Shell Nanocrystals with Photostability and Electronic Accessibility," *J. Am. Chem. Soc.*, 119(30):7019-7029, 1997.

Peng et al., "Synthesis and Isolation of a Homodimer of Cadmium Selenide Nanocrystals," *Angew. Chem. Int. Ed. Engl.*, 36(112):145-147, 1997.

Plunkett et al., "Combinatorial Chemistry and New Drugs" *Sci Am.*, 276(4):68-73, Apr. 1997.

Rogach et al., "Synthesis and Characterization of Thiol-Stabilized CdTe Nanocrystals" *Ber. Bunsenges. Phys. Chem.*, 100(11):1772-1778, Nov. 1996.

Schröck et al., "Multicolor Spectral Karyotyping of Human Chromosomes," *Science*, 273:494-497, Jul. 26, 1996.

Spanhel et al., "Photochemistry of Colloidal Semiconductors. Surface Modification and Stability of Strong Luminescing CdS Particles" *J. Am. Chem. Soc.*, 109(19):5649-5655, 1987.

Steigerwald et al., "Surface Derivatization and Isolation of Semiconductor Cluster Molecules," *J. Am. Chem. Soc.*, 110:3046-3050, 1988.

Whitesell et al., "Directionally Aligned Helical Peptides on Surfaces" *Science*, 261:73-76, Jul. 2, 1993.

Masumoto et al. "Preparation of Monodisperse CdS Nanocrystals by Size Selective Photocorrosion" *J. Phys. Chem.* 100(32):13782 (Aug. 1996).

Colvin et al. "Light-Emitting Diodes from Cadmium Selenide Nanocrystals and a Semiconducting Polymer" *Nature* 370:354 (Aug. 1994).

B.O. Dabbousi and M.G. Bawendi "Electroluminescence from CdSe Quantum-Dot/Polymer Composites" *Appl. Phys. Lett.* 66(11):1316 (Mar. 1995).

Kortan et al. "Nucleation and Growth of CdSe on ZnS Quantum Crystallite Seeds, and Vice Versa, in Inverse Micelle Media" *J. Am. Chem. Soc.* 112:1327 (1990).

Nirmal et al. "Fluorescence Intermittency in single Cadmium Selenide Nanocrystals" *Nature* 383:802 (Oct. 1996).

Murray et al. "Synthesis and Characterization of Nearly Monodisperse CdE (E=S, Se, Te) Semiconductor Nanocrystallites" *J. Am. Chem. Soc.* 115:8706 (1993).

Empedocles et al. "Photoluminescence Spectroscopy of Single CdSe Nanocrystallite Quantum Dots" *Phys. Rev. Lett.* 77(18):3873 (Oct. 1996).

M.A. Hines and P. Guyot-Sionnest "Synthesis and Characterization of Strongly Luminescing ZnS-Capped CdSe Nanocrystals" *J. Phys. Chem.* 100:468 (Jan. 1996).

A.P. Alivisatos "Perspectives on the Physical Chemistry of Semiconductor Nanocrystals" *J. Phys. Chem.* 100:13226 (Aug. 1996).

Rajh, et al., "Synthesis and Characterization of Surface-Modified Colloidal CdTe Quantum Dots," *J. Phys. Chem.* 97:11999-12003, Nov. 1993.

Lawless, et al., "Bifunctional Capping of CdS Nanoparticles and Bridging to $TiO_2$," *J. Phys. Chem.* 99:10329-10335, 1995.

Gan, et al., "Enhanced Photoluminescence and Characterization of Mn-Doped ZnS Nanocrystallites Synthesized in Microemulsion," *Langmuir* 1997(13):6427-6431, 1997.

Kuno, et al., "The band edge luminescence of surface modified CdSe nanocrystallites: Probing the luminescing state," *J. Chem. Phys.* 106(23):9869-9882, Jun. 1997.

"Strongly Photoluminescent CdTe Nanocrystals by Proper Surface Modification," M. Gao et al., *J. Phys. Chem. B.* 102:8360-8363 (1998).

"Photochemistry and Radiation Chemistry of Colloidal Semiconductors. 33. Chemical Changes and Fluorescence in CdTe and ZnTe," U. Resch et al., *Langmuir* 5:1015-1020 (1989).

"An EXAFS Study on Thiolclapped CdTe Nanocrystals," J. Rockenberger et al., *Ber. Bunsenges. Phys. Chem.* 102:1561-1564 (1998).

"Synthesis, Morphology and Optical Properties of Thiol-Stabilized CdTe Nanoclusters in Aqueous Solution," A. L. Rogach et al., *Ber. Bunsenges. Phys. Chem.* 101:1668-1670 (1997).

"Micro photoluminescence spectra of CdTe and CdMnTe self-organized quantum dots," T. Kuroda et al., *Journal of Luminescence* 83-84:321-342 (1999).

"Quantum confinement effects on the optical phonons of CdTe quantum dots," A.M. De Paula et al., *Superlattices and Microstructures* 23:1103-1106 (1998).

"Probing of the quantum dot size distribution in CdTe-doped glasses by photoluminescence excitation spectroscopy," C.R.M. de Oliveira et al., *Appl. Phys. Lett.* 66:439-441 (1995).

"Synthesis and Characterization of Thiol-Stabilized CdTe Nanocrystals," A.L. Rogach et al., *Ber. Bunsenges. Phys. Chem.* 100:1772-1778 (1996).

"Synthesis and Characterization of Surface-Modified Colloidal CdTe Quantum Dots," T. Rajh et al., *J. Phys. Chem.* 97:11999-12003 (1993).

"Nanoparticle precursor route to low-temperature spray deposition of CdTe thin films," M. Pehnt et al., *Appl. Phys. Lett.* 67:2176-2178 (1995).

"Characterization of Solution-Synthesized CdTe and HgTe," M. Müllenborn et al., *Applied Physics* A56:317-321 (1993).

"Solution Synthesis and Photoluminenscence Studies of Small Crystallites of Cadmium Telluride," R. F. Jarvis, Jr. et al., *Mat. Res. Soc. Symp. Proc.*, 272:229-235 (1992).

C.B. Murray et al.; "Synthesis and Characterization of Nearly Monodisperse CdE (E=S,Se,Te) Semiconductor Nanocrystallites"; *J. Am. Chem. Soc 115*; pp. 8709-8715 (1993).

Database Crossfire Online!; Beilstein Institut zur Forderung der Chemischen Wissenschaft; Beilstein Registry Nos. 2097823 and 1860016; XP002152687—Abstract.

Ekimov, A.I. et al., "Growth and optical properties of semiconductor nanocrystals in a glass matrix," *Journal of Luminescence* 70 (1996) 1-20.

* cited by examiner

FIG. 1(b)
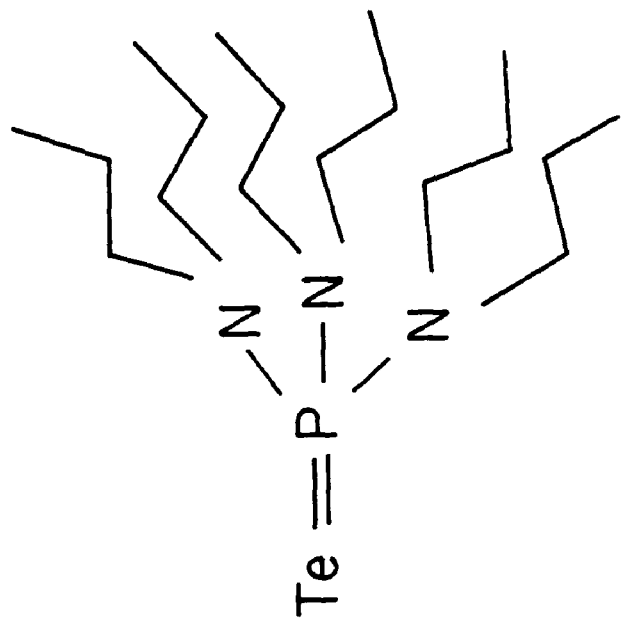
hexapropylphosphorustriamide telluride
HPPTTe
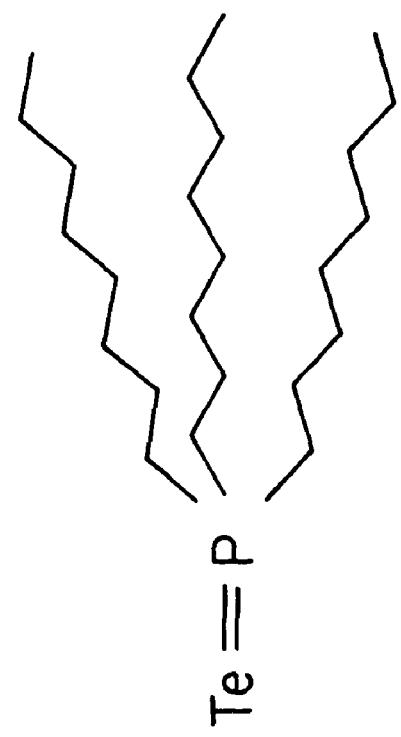
trioctylphosphine telluride
TOPTe

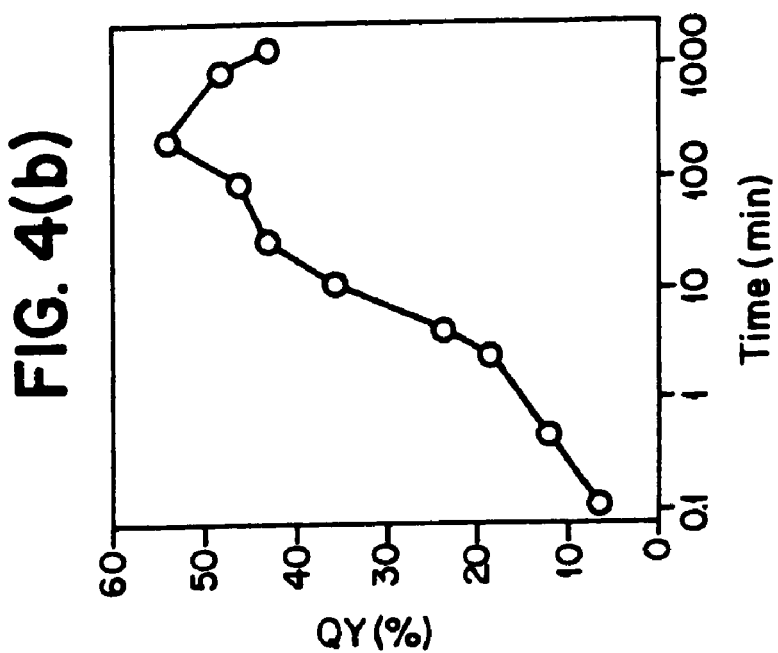
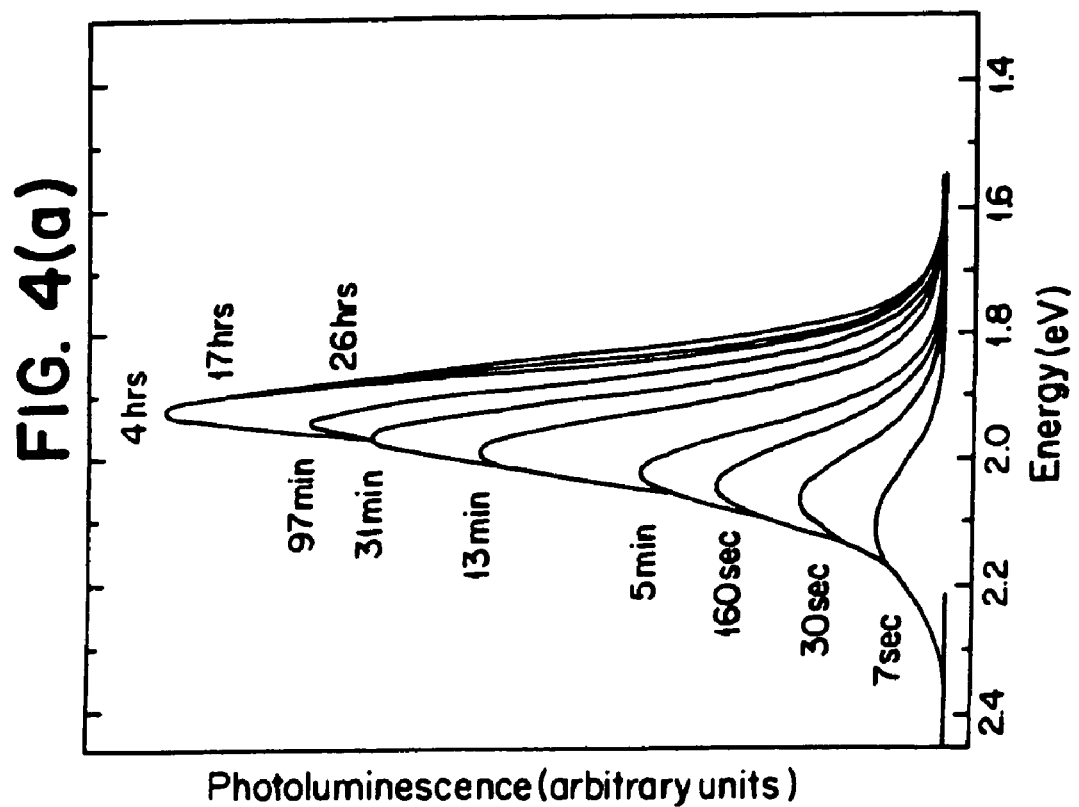

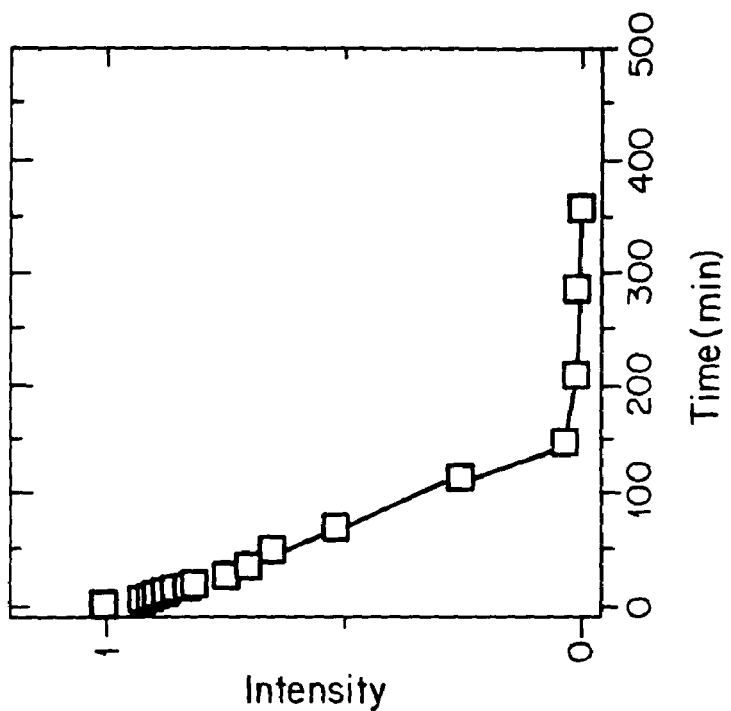
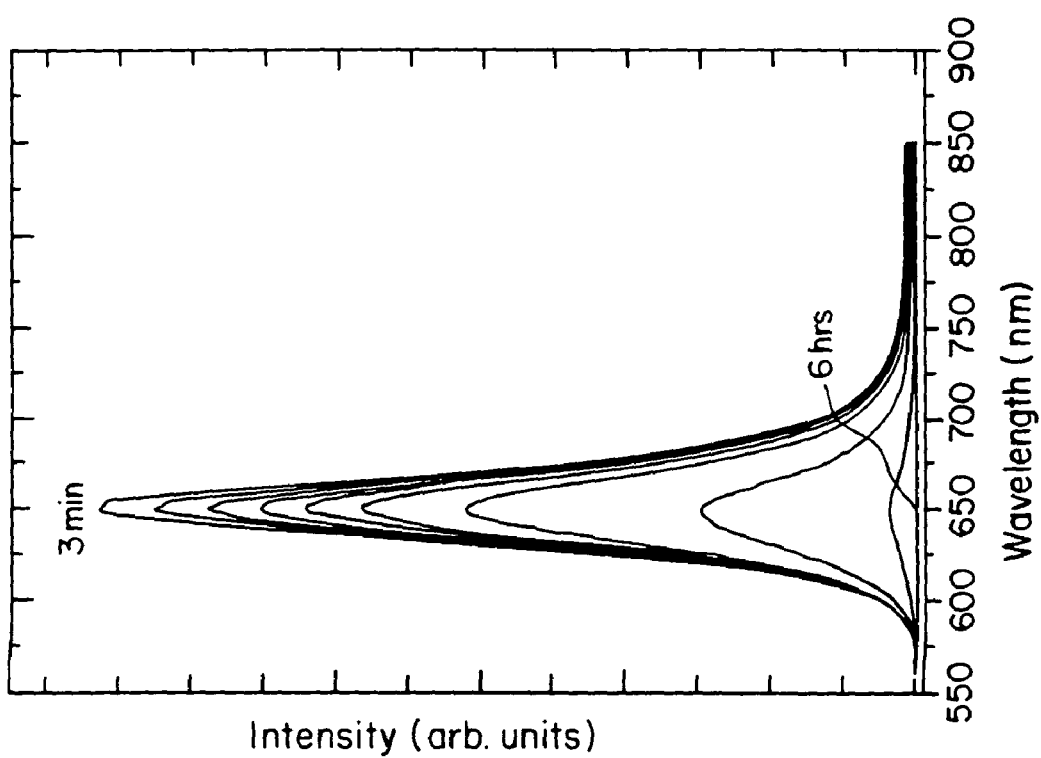

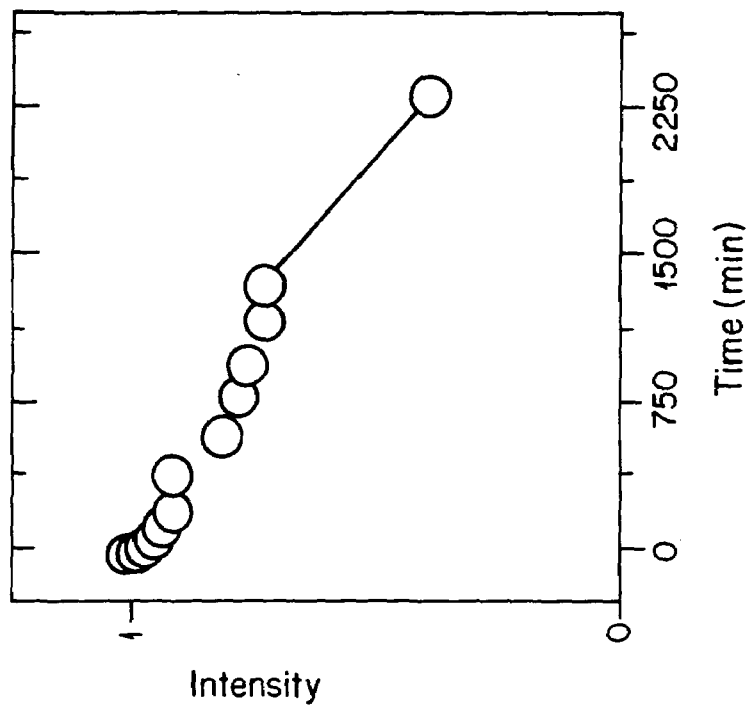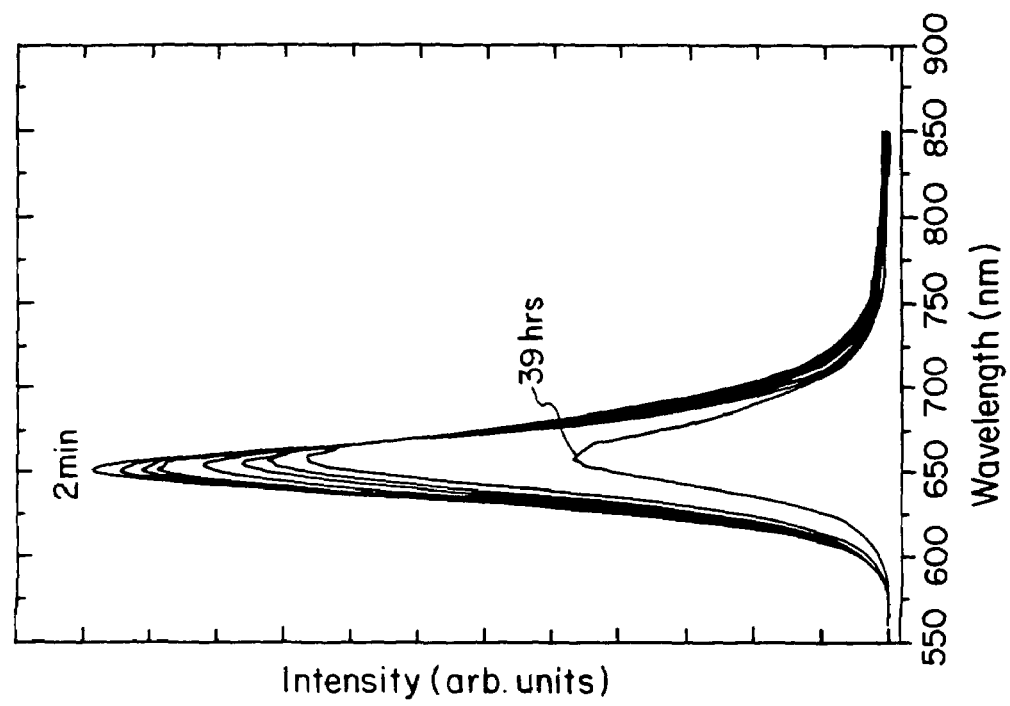

TELLURIUM-CONTAINING NANOCRYSTALLINE MATERIALS

CLAIM OF PRIORITY

This application is divisional of, and claims priority to, U.S. patent application Ser. No. 09/625,861, filed on Jul. 26, 2000, now U.S. Pat. No. 6,607,829 which claims priority to U.S. Patent Application Ser. No. 60/145,708, filed on Jul. 26, 1999, and is a continuation-in-part of U.S. patent application Ser. No. 08/969,302, filed Nov. 13, 1997, now U.S. Pat. No. 6,322,901, each of which is hereby incorporated by reference in its entirety.

FEDERALLY SPONSORED RESEARCH OR DEVELOPMENT

This invention was made with government support under Contract No. DMR-94-00334 from the National Science Foundation. The government has certain rights in the invention.

TECHNICAL FIELD

The invention relates to tellurium-containing nanocrystalline materials, and to methods for making such materials.

BACKGROUND

Semiconductor nanocrystallites having radii smaller than the bulk exciton Bohr radius constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of nanocrystallites shift to the blue (i.e., to higher energies) as the size of the crystallite gets smaller.

Bawendi and co-workers have described a method of preparing monodisperse semiconductor nanocrystallites by pyrolysis of organometallic reagents injected into a hot coordinating solvent (*J. Am. Chem. Soc.*, 115:8706 (1993)). This permits temporally discrete nucleation and results in the controlled growth of macroscopic quantities of nanocrystallites. The particle size distribution can be refined by size selective precipitation. The narrow size distribution of nanocrystallites can allow the particles to have narrow spectral width emissions. These techniques can yield excellent results in the production of selenium-containing II-VI semiconductor nanocrystallites.

SUMMARY

The invention provides methods of synthesizing telluride semiconductor nanocrystallites. The nanocrystallites can have high quantum efficiencies and can have narrow size distributions. The telluride semiconductors have relatively smaller band gaps than their selenide and sulfide analogs, and can expand the range of colors available using II-VI photoluminescent nanocrystallites further into the far red range of the spectrum. In particular, cadmium telluride nanocrystallites can emit in wavelengths sufficiently long to make them suitable for use in multicolor detection schemes for whole blood diagnostics, where emission wavelengths of at least 630 nm can be preferred.

In one aspect, the invention features a nanocrystallite including a core of MTe, where M is cadmium, zinc, magnesium, mercury, or mixtures thereof. The core can have an overcoating on a surface of the core. The overcoating can be a semiconductor having a composition different from the core.

In another aspect, the invention features a nanocrystallite including MTe that can photoluminesce with a quantum efficiency of at least 20%.

In another aspect, the invention features a method of manufacturing nanocrystallites by injection of an M-containing compound, M being cadmium, zinc, magnesium, mercury, or mixtures thereof, and a Te-containing compound of the form

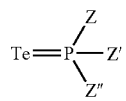

where at least one of Z, Z', and Z" is an amide. Preferably, two of Z, Z', and Z" are, independently, amides, and more preferably three of Z, Z', and Z" are, independently, amides. The mixture is heated to grow the nanocrystallites. The heating can be controlled in such a way that the growth is controlled. The M-containing compound and a Te-containing compound can be premixed, or M and Te can be incorporated into different positions of a single molecule. The M-containing compound and the Te-containing compound can be injected sequentially or simultaneously. Additional M-containing compound, additional Te-containing compound, or a mixture thereof, can be added to the mixture during heating. An overcoating can be grown on a surface of the nanocrystallite. The nanocrystallites can be separated by size selective precipitation. An amine can be added to the mixture during size selective precipitation. The Te-containing compound can include a tris(dialkylamino)phosphine telluride. The Te-containing compound can have a boiling point of at least 200° C., preferably 250° C., and more preferably 280° C., at one atmosphere.

In another aspect, the invention features a Te-containing compound of the form

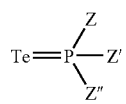

where at least one of Z, Z', and Z" is an amide, and a method of preparing a Te-containing compound including contacting P(Z)(Z')(Z") with Te.

The nanocrystallite can have a quantum efficiency of emission of at least 30%, 40%, 50%, 60%, or 70%. The quantum efficiency can be as high as 75%, 80%, 90%, 95% or 99%. The quantum efficiency can be between 20 and 99%, preferably between 30 and 99%, more preferably between 40 and 95%, and most preferably between 70 and 95%. The nanocrystallite can be a member of a size-selected population having no more than a 15% RMS deviation from mean diameter, preferably 10% RMS deviation or less, and more preferably 5% RMS deviation or less. CdTe nanocrystallites can photoluminesce and can have emission wavelengths in the range of 580 to 770 nm, preferably 550 to 780 nm, and more preferably 435 to 800 nm. The nanocrystallite can photoluminesce with a full-width at half maximum (FWHM) of 70 nm or less, preferably 45 nm or less, more preferably 20 nm or less, and most preferably 15 nm or less for a single nanocrystallite.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1(b) is a drawing depicting structures of two precursors for synthesis of CdTe nanocrystals.

FIG. 4 is a graph depicting the evolution of photoluminescence during nanocrystallite synthesis.

FIG. 6 is a graph depicting the evolution of the photoluminescence of a dilute solution of nanocrystallites exposed to air.

FIG. 7 is a graph depicting the evolution of the photoluminescence of a dilute solution of nanocrystallites in an air-free environment.

DETAILED DESCRIPTION

Tellurium-containing nanocrystallites can be produced by injection of an M-containing compound and a Te-containing compound into a hot coordinating solvent, followed by growth and annealing of the nanocrystallites. The nanocrystallites can include CdTe, ZnTe, MgTe, HgTe, or alloys thereof. By proper selection of precursor composition and stoichiometry, telluride semiconductor photoluminescent nanocrystallites having quantum efficiencies as high as 70% can be produced.

Improved telluride nanocrystallites can be produced by varying the precursor compounds and the precursor stoichiometry from that described in U.S. patent application Ser. No. 08/969,302, filed Nov. 13, 1997, which is incorporated herein by reference in its entirety. Cadmium telluride nanocrystallites made by the methods described in U.S. application Ser. No. 08/969,302 using dimethyl cadmium ($Me_2Cd$) and trioctylphosphine telluride (TOPTe) as precursors exhibit inefficient photoluminescence, having quantum efficiencies of less than 1%. The telluride-containing nanocrystallites produced using a Te-containing compound including an amino group can be prepared having quantum efficiencies as high as 70%, more than threefold higher than the quantum efficiency of 20% reported for colloidal CdTe nanocrystallites (J. Phys. Chem. 1993(97):11999–12003). The quantum efficiency of nanocrystallites can be further enhanced by overcoating a core nanocrystallite with a layer of a second semiconductor material (e.g., ZnS or ZnSe overcoated CdTe cores).

Tellurium-containing nanocrystallites are obtained using a high temperature colloidal growth process, preferably followed by size selective precipitation. The high temperature colloidal growth process can be accomplished by rapidly injecting an appropriate combination of an M-containing compound and Te-containing compound into a hot coordinating solvent to produce a temporally discrete homogeneous nucleation and controlling the growth of the nuclei into nanocrystallites. Injection of reagents into the hot reaction solvent results in a short burst of homogeneous nucleation. This temporally discrete nucleation is attained by a rapid increase in the reagent concentration upon injection, resulting in an abrupt supersaturation, which is relieved by the formation of nuclei and followed by growth on the initially formed nuclei. The partial depletion of reagents through nucleation and the sudden temperature drop associated with the introduction of room temperature reagents prevents further nucleation.

Figure 1A:
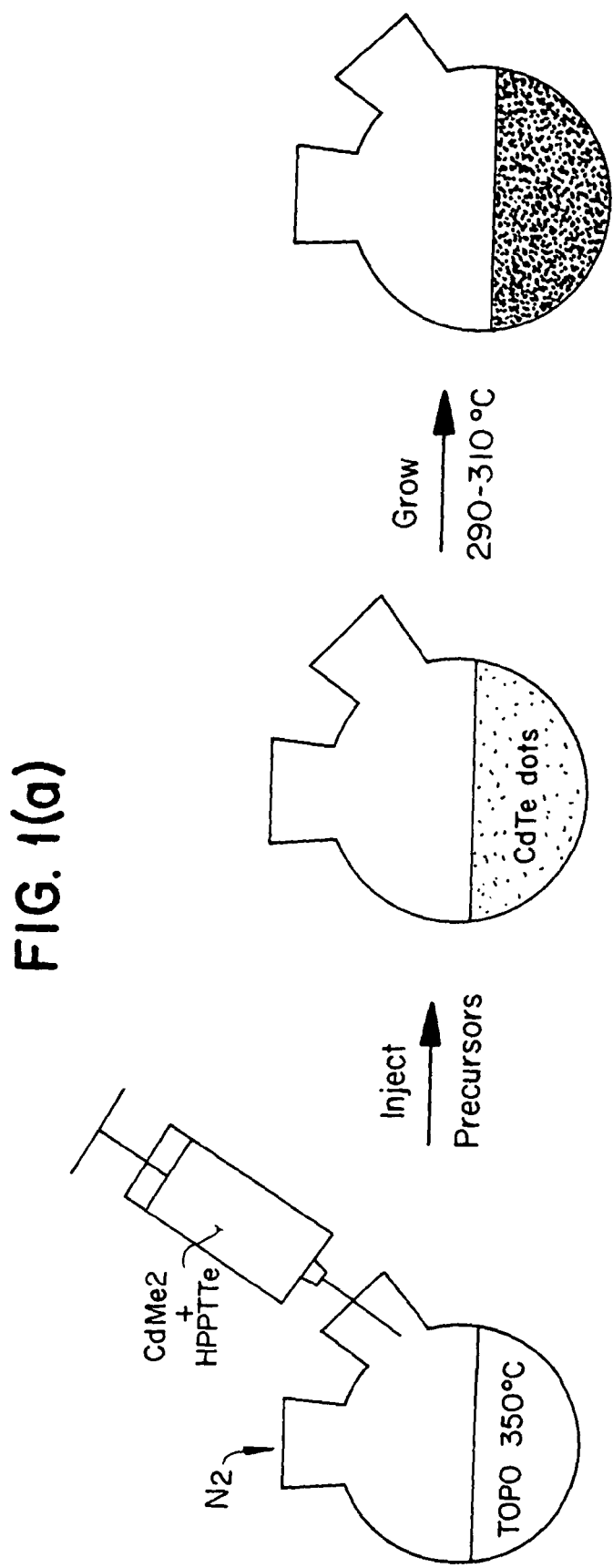
FIG. 1(a) is a diagram depicting a method according to the invention.

The solution then may be gently heated to reestablish the solution temperature. Gentle reheating allows for growth and annealing of the nanocrystallites. The higher surface free energy of the small crystallites makes them less stable with respect to dissolution in the solvent than larger crystallites. The net result of this stability gradient is the slow diffusion of material from small particles to the surface of large particles ("Ostwald ripening"). In addition, the reagents remaining in the coordinating solvent may contribute to growth; this effect may be encouraged by feeding additional reagents to the solution during growth. Growth and ripening of this kind result in a highly monodisperse colloidal suspension from systems which may initially be highly polydisperse. The process of slow growth and annealing of the nanocrystallites in the coordinating solvent that follows nucleation results in uniform surface derivatization and regular core structures. Both the average size and the size distribution of the crystallites in a sample are dependent on the growth temperature. The growth temperature necessary to maintain steady growth increases with increasing average crystal size. As the size distribution sharpens, the temperature may be raised to maintain steady growth. The growth period may be shortened significantly by using a higher temperature or by adding additional precursor materials. The overall process is shown schematically in FIG. 1(a).

Size distribution during the growth stage of the reaction can be estimated by monitoring the absorption line widths of the particles. Modification of the reaction temperature in response to changes in the absorption spectrum of the particles allows the maintenance of a sharp particle size distribution during growth. Reactants can be added to the nucleation solution during crystal growth to grow larger crystals. The photoluminescence (PL) spectra of the nanocrystallites can be tuned continuously over maximum emission wavelengths from 550 to 780 nm, complementing the available wavelengths for nanocrystallites having CdSe cores. The wavelength of maximum emission can be tuned by stopping the growth a particular average size of nanocrystallite. The particle size distribution may be further refined by size selective precipitation.

The M-containing compound can be an organometallic compound, such as an alkyl-M compound. For example, the M-containing compound can be MRQ wherein M is Cd, Zn, Hg or Mg, and R and Q are, independently, alkyl, alkenyl, aryl, cycloalkyl, or cycloalkenyl. Preferred examples include dialkyl Cd, dialkyl Zn, dialkyl Hg or dialkyl Mg.

The Te-containing compound can be a stable phosphine telluride, preferably a tris amido phosphine telluride. The Te-containing compound can have formula

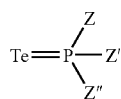

At least one of Z, Z', and Z" can be an amide. Preferably, two of Z, Z', and Z" are amides. The remaining groups of Z, Z', and Z" can be alkyl, alkenyl, aryl, cycloalkyl, or cycloalkenyl, or derivatives thereof. More preferably, each of Z, Z', and Z" is an amide. Each of Z, Z', and Z" can have the formula —N(A)(A'), where each of A and A', independently, is alkyl, alkenyl, aryl, cycloalkyl, or cycloalkenyl, or a derivative thereof. Preferably, each of Z, Z', and Z" is a dialkyl amide. Each alkyl can be a lower alkyl. The Te-containing compound has a boiling point of at least 200° C. One suitable Te-containing compound is hexapropylphosphorustriamide telluride (HPPTTe). HPPTTe produces unexpectedly high quantum efficiency nanocrystallites as compared nanocrystallites prepared from trioctylphosphine telluride (TOPTe). The structures of HPPTTe and TOPTe are shown in FIG. 1(b).

Alternatively, a single compound containing M and Te can be used as both the M-containing compound and the Te-containing compound. An example of such a compound is a Te-containing compound in which one of Z, Z', and Z" includes a dialkyl M moiety.

Alkyl is a branched or unbranched saturated hydrocarbon group of 1 to 100 carbon atoms, preferably 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" includes an alkyl group of 1 to 20 carbon atoms, preferably 2 to 8 carbon atoms.

Alkenyl is a branched or unbranched hydrocarbon group of 2 to 100 carbon atoms containing at least one carbon-carbon double bond, such as ethenyl, n-propenyl, isopropenyl, n-butenyl, isobutenyl, t-butenyl, octenyl, decenyl, tetradecenyl, hexadecenyl, eicosenyl, tetracosenyl and the like. The term "lower alkenyl" includes an alkenyl group of 2 to 20 carbon atoms, preferably 2 to 8 carbon atoms, containing one —C=C— bond.

Optionally, an alkyl, or alkenyl chain can contain 1 to 6 linkages selected from the group consisting of —O—, —S—, -M- and —NR— where R is hydrogen, lower alkyl or lower alkenyl.

Aryl is a monovalent aromatic hydrocarbon radical consisting of one or more fused rings in which at least one ring is aromatic in nature, which can optionally be substituted with one or more of the following substituents: hydroxy, cyano, alkyl, alkoxy, thioalkyl, halo, haloalkyl, hydroxyalkyl, nitro, amino, alkylamino, and dialkylamino, unless otherwise indicated.

Cycloalkyl is reference to a monovalent saturated carbocyclic radical consisting of one or more rings, which can optionally be substituted with one or more of the following substituents: hydroxy, cyano, alkyl, alkoxy, thioalkyl, halo, haloalkyl, hydroxyalkyl, nitro, amino, alkylamino, and dialkylamino, unless otherwise indicated.

Cycloalkenyl includes reference to a monovalent unsaturated carbocyclic radical consisting of one or more rings and containing one or more carbon-carbon double bonds, which can optionally be substituted with one or more of the following substituents: hydroxy, cyano, alkyl, alkoxy, thioalkyl, halo, haloalkyl, hydroxyalkyl, nitro, amino, alkylamino and dialkylamino, unless otherwise indicated.

The absolute quantum efficiency of the nanocrystallites was as high as 70%. The average quantum efficiency of a group of 15 nanocrystallite samples was 60±5%, attesting to the reproducibility of the method. FIG. 2 displays UV/vis absorption spectra from CdTe preparations using (a) TOPTe and (b) HPPTTe. Initial absorption spectra from each reaction show similar qualitative features. Nucleation produces a bimodal distribution of sizes, with the smaller species quickly dissolving into feedstock for the larger nanocrystallites. After three hours of stirring at 290° C., each reaction has effectively the same absorption spectrum. As monitored by absorption spectroscopy, both reactions appear the same. However, the quantum efficiency of the CdTe synthesized with TOPTe is only 1%, whereas the quantum efficiency of CdTe produced with HPPTTe is 55%.

Without wishing to be bound by any particular explanation, it is believed that the strong electron-donating properties of the amide groups in the HPPTTe are at least partially responsible for the improvement in nanocrystal quality. Te-containing compounds having one or two amide groups can produce significantly improved quantum efficiencies for telluride nanocrystallites compared to trialkyl phosphine telluride compounds. A suitable Te-containing compound should be stable at reaction temperature (e.g., having a boiling point of at least 200° C.).

Figure 2A:
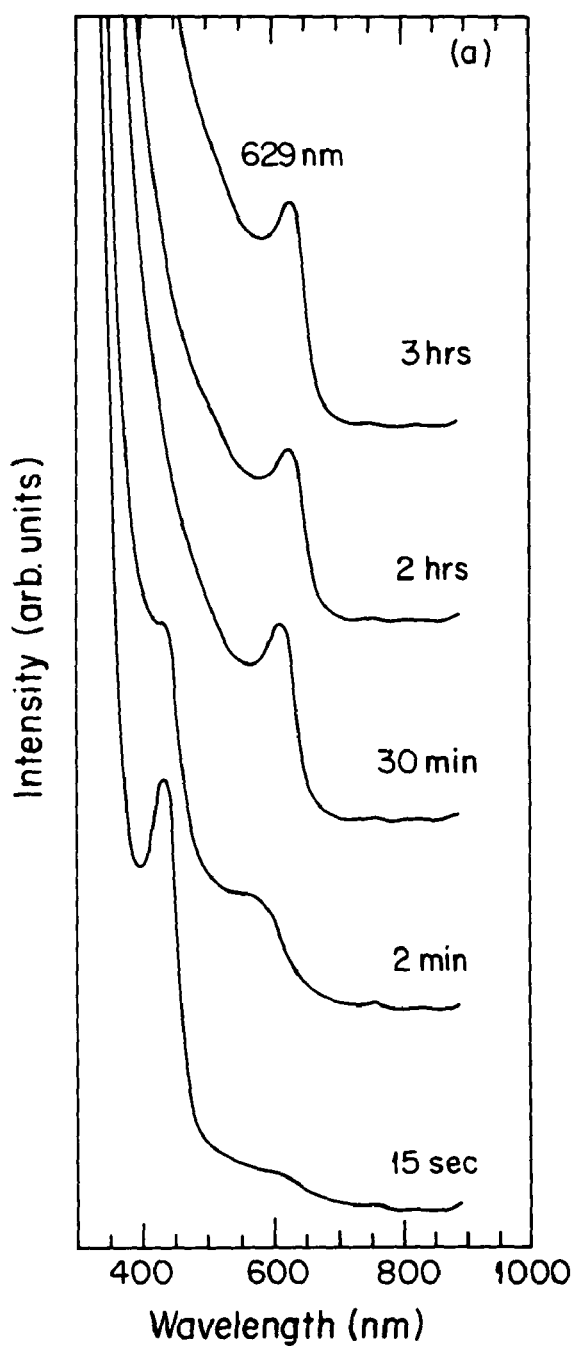
FIGS. 2(a)–2(c) are graphs depicting the UV/vis absorption spectra and the x-ray diffraction spectra of CdTe nanocrystals prepared with TOPTe and HPPTTe.
Figure 2B:
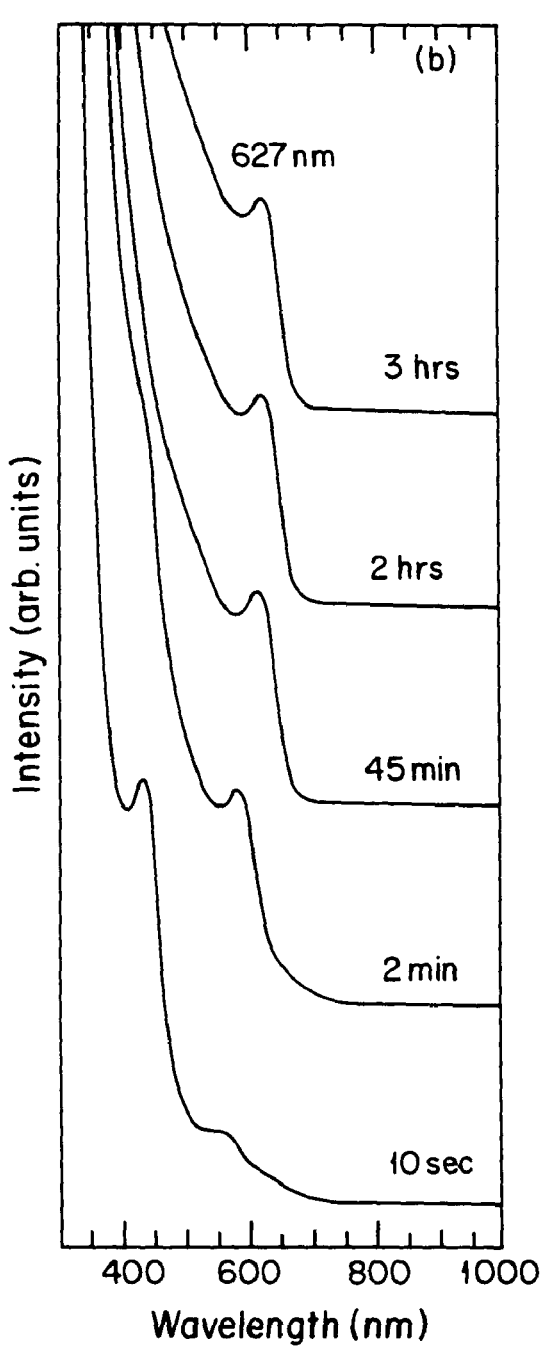
Figure 2C:
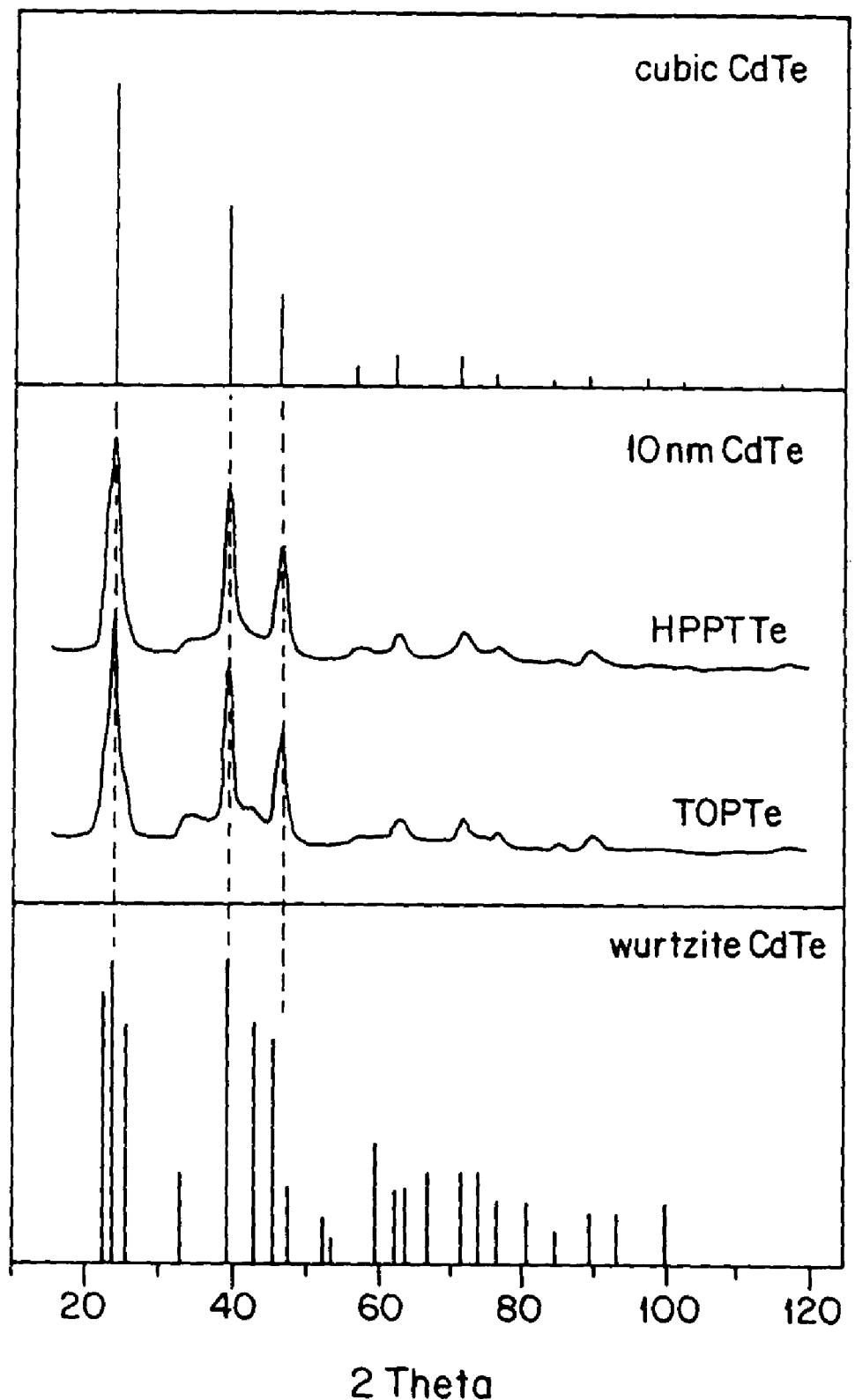

The interchangeability of the spectra of FIGS. 2(a) and 2(b) suggests that UV/vis absorption spectroscopy is not sensitive to the differences which would explain the PL intensities. TEM and XRD analysis also did not reveal any substantial differences between the two species, as shown by the XRD spectra in FIG. 2(c).

The nanocrystallites can be overcoated with a coating of a semiconductor material. For example, ZnS, ZnSe or CdSe overcoatings can be grown on CdTe nanocrystallites.

The telluride nanocrystallites can be suitable for a variety of applications, including those disclosed in copending and commonly owned U.S. Pat. Nos. 6,251,303 and 6,326,144, and U.S. application Ser. No. 09/160,458, filed Sep. 24, 1998, each of which is incorporated herein by reference in their entirety.

EXAMPLES

Synthesis of CdTe Nanocrystallites

Unless otherwise noted, all reactions were carried out in a dry nitrogen atmosphere using a glovebox or standard Schlenk techniques. HPLC grade solvents used for size selective precipitation were purged of dissolved oxygen by bubbling with nitrogen for 5 minutes. Trioctylphosphine (TOP, 95%) was used as received from Fluka. Tellurium shot (99.999%, low oxide) was used as received from Alfa/Aesar. Hexa-n-propyl phosphorous triamide (HPPT, 97%, Lancaster) was vacuum distilled, collecting the fraction boiling between 83–103° C. at 0.55 Torr. Trioctylphosphine oxide (TOPO, 90%, Strem) was dried under vacuum (~0.5 Torr) for 1 hour. Dimethyl cadmium (99+%, Strem) was purified by vacuum transfer.

A stock solution of hexapropylphosphorustriamide telluride (HPPTTe) was prepared by adding 6.38 g tellurium shot to 45.00 g HPPT and stirring until dissolved (1–2 days). 20 g TOPO was dried under vacuum (~0.5 Torr) at 180° C. for 1 hour, then filled with $N_2$ and heated to 350° C. In a $N_2$ atmosphere glovebox a solution containing 50 μL $CdMe_2$ (0.69 mmol), 0.35 mL HPPTTe stock (0.35 mmol), and 12 mL TOP was mixed very well and loaded into a syringe. This solution was smoothly injected (~0.5 sec) into the vigorously stirring TOPO, which immediately turned red and cooled to 270° C. When the reaction solution was sampled within 20 seconds of injection, the initial UV/vis spectrum displayed a bimodal distribution of sizes, with absorption features at 435 and 560 nm. Subsequent absorption spectra showed no evidence of a high energy peak, with the first absorption feature now peaked at 580 nm. The temperature was raised to 290° C. and the sample was grown to the desired wavelength. The flask was then cooled to ~60° C. and mixed with 10 mL butanol. This solution can be stored (under nitrogen) for at least 6 months without noticeable decrease in quantum efficiency.

Nanocrystallites were isolated in air by a modified size selective precipitation with acetonitrile. The reaction solution prepared above was mixed with an additional 10 mL butanol. Acetonitrile was added until the mixture became turbid. Upon sitting for a few minutes the solution separated into two layers. The colorless hydrophilic phase was then removed and discarded. The clear red hydrophobic phase was mixed with approximately one third its original volume of butanol. The process of adding acetonitrile until turbidity and separating layers was repeated until a powder or very thick oil was obtained. Freshly prepared CdTe nanocrystallites isolated in this fashion are moderately soluble in hexane and extremely soluble in tetrahydrofuran (THF). Addition of a small amount of TOP (~1% vol) helped preserve the luminescence intensity of the size selected material. Yields of crude CdTe ranged from 50 mg (small sizes) to 75 mg (large sizes) of dry powder.

Figure 3A:
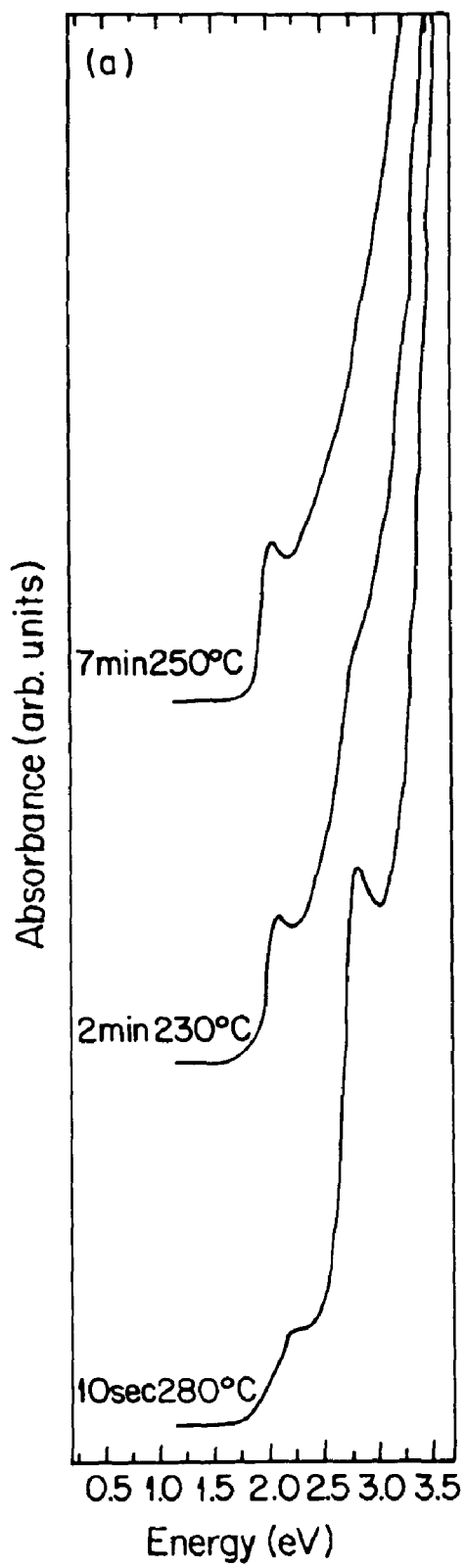
FIGS. 3(a) and 3(b) are graphs depicting the development of the UV/vis absorption spectra during nanocrystallite synthesis.

CdTe nanocrystallites were synthesized using a method that employed a 1M hexapropyl phosphorous triamide telluride (HPPTTe) solution as the chalcogenide-containing compound. Distillation of the HPPT before use was found to significantly increase the quantum efficiency of the samples. Purification of $CdMe_2$ by vacuum transfer gave more consistent results than filtration through 0.2 μm PTFE membrane. Also, a cadmium rich preparation was found to give better results. The optimum Cd:Te injection solution ratio for the conditions of this example was determined empirically to be 2:1. FIG. 3 displays UV/vis absorption spectra at various times during CdTe synthesis. FIG. 3(a) highlights the early stages of the synthesis. The bottom spectrum of FIG. 3(a), taken 10 seconds after injection when the temperature had fallen to 280° C., shows that the reaction solution contained a bimodal distribution of sizes. Well defined features at 2.23 eV (566 nm) and 2.84 eV (437 nm) are clearly visible. A species absorbing at or near 435 nm can be synthesized by performing the injection at 200° C. or below. These are the smallest nanocrystallites to display a nanocrystallite-like absorption and appear to be the 435 nm-absorbing CdTe species equivalent to 410 nm absorption CdSe. Two minutes into the reaction the concentration of this 435 nm-absorbing CdTe species was greatly reduced, and at 7 minutes there was no trace of this species. These 435 nm-absorbing CdTe species did not appear to be growing. No spectral feature has been observed between 435 and 550 nm during reactions performed under similar initial conditions. Instead, the 435 nm-absorbing CdTe species appeared to be dissolving as the absorption of the larger nanocrystallites grew and sharpened. Growth of the larger particles at the expense of the smaller ones is an Ostwald ripening mechanism and is to be expected given the difference in size (~35 Å versus ~15 Å). The observation of this mechanism would not be noteworthy, except for the fact that in this case the dissolving species is the 435 nm-absorbing CdTe species. The other semiconductor materials in this family, CdS and CdSe, do not show similar behavior in their growth pattern.

Characterization of Nanocrystallites

UV/visible absorption spectroscopy of CdTe nanocrystallites in hexane was performed on an HP 8453 diode array spectrometer with 1 nm resolution. Fluorescence measurements were made using a SPEX Fluorolog-2 spectrofluorometer which consisted of two double monochromators with 2400 grooves/inch gratings blazed at 500 nm and photomultiplier tube (R928) detector. CdTe samples were dissolved in either hexane or THF with ~1% TOP in a 1 cm quartz cuvette and diluted until the absorbance of the first feature was below 9.3. Spectra were obtained in front face geometry and were corrected for the wavelength dependence of the optics and detector by multiplication with a suitable correction factor file (MCOR1097.SPT).

Figure 3B:
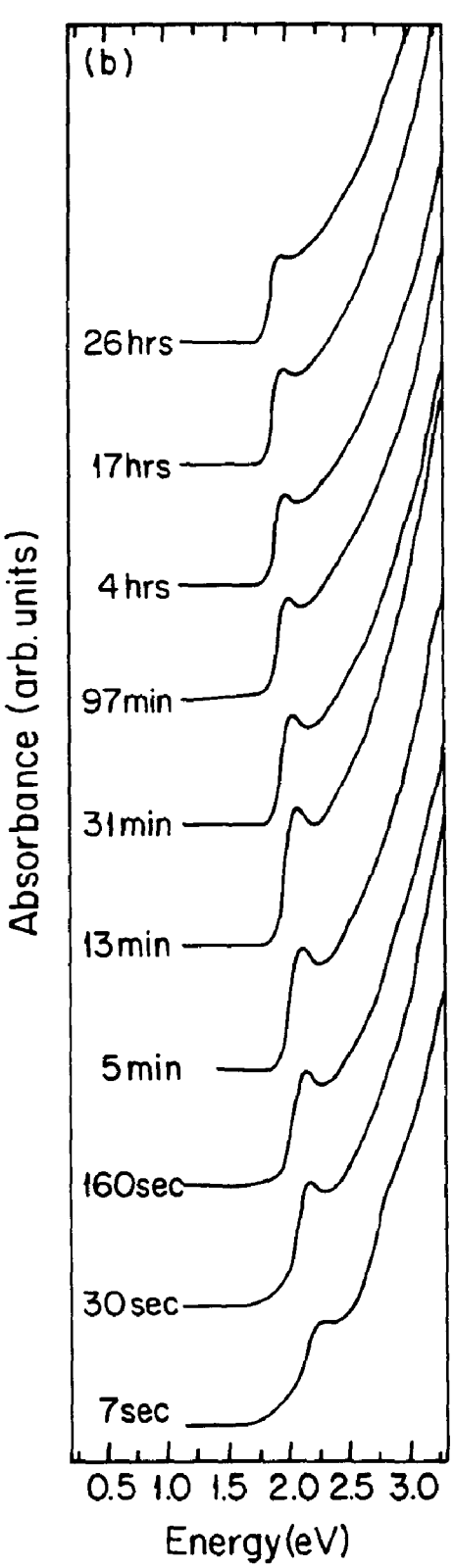

FIG. 3(b) displays absorption spectra of aliquots taken from a single synthesis of CdTe. A well defined first absorbing state is visible in all spectra, indicating that the growth is controlled. FIG. 4 shows the corresponding photoluminescence (PL) emission spectra for the same reaction. Spectra have been standardized relative to a methanol solution of rhodamine 640 (quantum efficiency=100%) so as to accurately reflect the emission intensity at various points during the reaction, a relationship which is plotted in the inset FIG. 4(b). Three features stand out in FIG. 4. First, the quantum efficiency improved over time. This result suggests the importance of an annealing effect. For small nanocrystallites it can be experimentally difficult to separate thermal annealing from particle growth. Second, all emission occurred at the band edge. There was no low energy (or deep trap) light detected for this size range. The spectral window was examined down to 1.18 eV (1050 nm) using a CCD detector without observing deep trap emission. More importantly, CdTe samples as small as ~35 Å diameter displayed no deep trap emission, whereas similarly sized CdS and CdSe luminescence spectra generally contain at least 20% deep trap emission. The third aspect of the emission is simply the sheer magnitude of the quantum efficiency. The nanocrystals used to generate FIG. 4 reaches 55%, but samples as high as 70% have been prepared.

Figure 5:
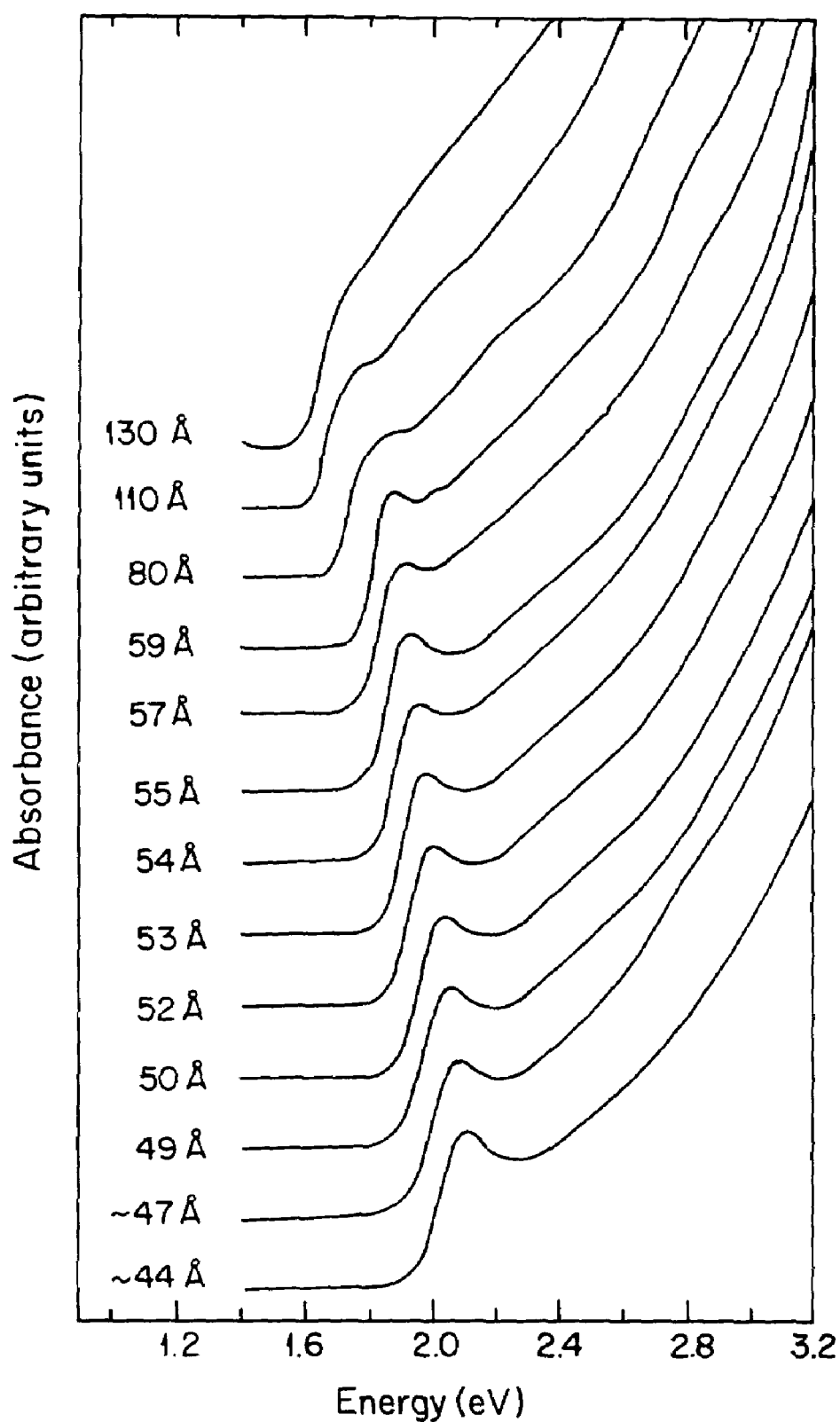
FIG. 5 is a graph depicting shows the accessible absorption spectra for CdTe nanocrystallites.

FIG. 5 presents absorption spectra illustrating the range of CdTe sizes that have been produced by this method. Any size/energy between the two extremes can be produced. Slight adjustments in starting material concentration and/or reaction temperature should enable the lower diameter limit to be reduced below its present value of ~44 Å.

Figure 8:
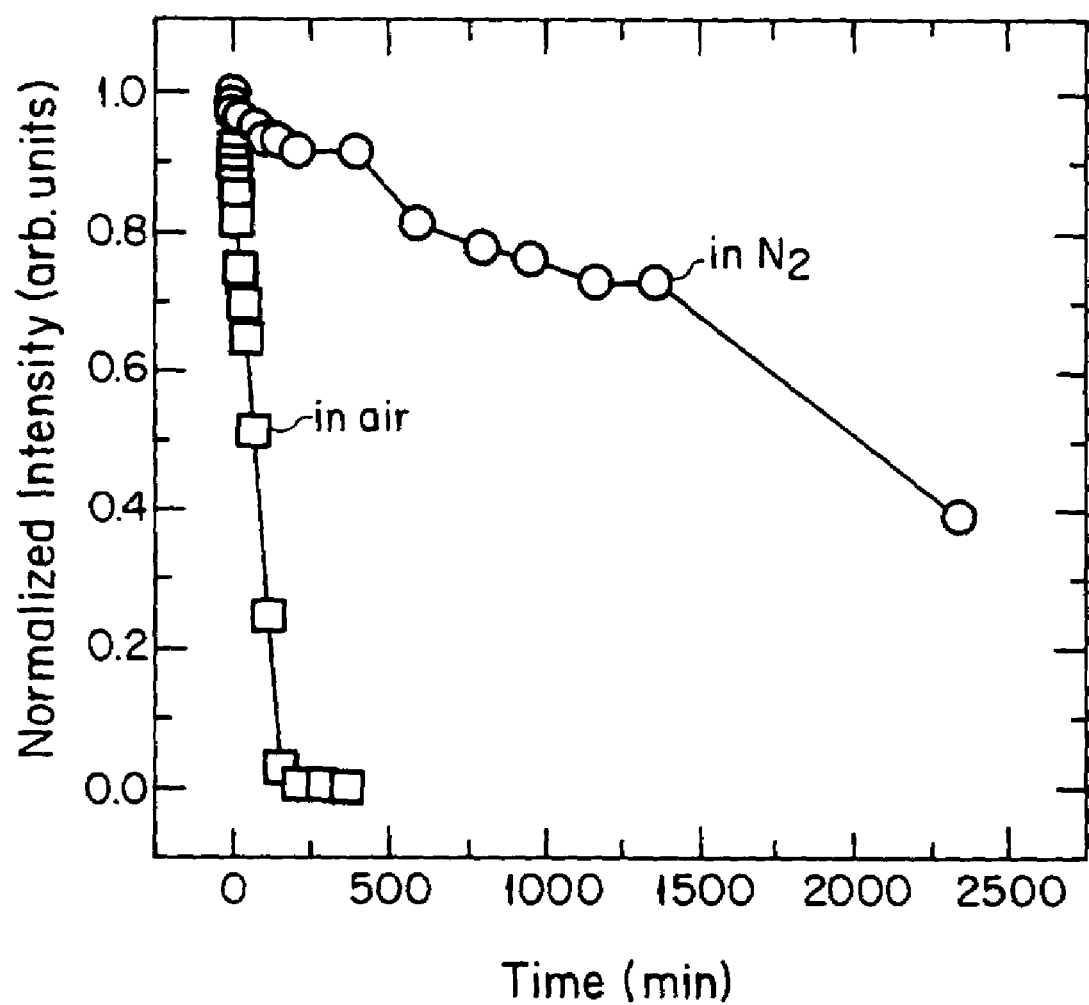
FIG. 8 is a graph depicting the intensity lifetimes of CdTe nanocrystallites stored under air and under nitrogen.

The stability with respect to flocculation and PL intensity of dilute solutions of CdTe nanocrystallites were qualitatively less than those of CdSe because the CdTe nanocrystallites are air sensitive. FIG. 6 shows the PL of a dilute hexane solution of 53 Å diameter CdTe as the emission decreases over time in air. The insert of FIG. 6 plots intensity versus time over the entire experiment. The emission intensity is effectively zero after 2.5 hours. At this point the solution is also quite turbid. A comparative experiment was conducted under nitrogen and the results are shown in FIG. 7. Even after 39 hours the fluorescence intensity has only fallen to just under half the initial value. Also, after 12 hours the air-free solution becomes very turbid. The solution phase "lifetimes" of the PL intensities are compared in FIG. 8. Results presented here show that the useable lifetime of CdTe nanocrystallites, particularly in dilute solutions, can be greatly extended by keeping the nanocrystallites in an inert atmosphere. While manipulating more concentrated solutions in air, for example, during size selective precipitation, PL does not appear to be greatly diminished. Long term storage of the nanocrystallites under nitrogen, or another inert gas, can help maintain the quantum efficiency.

Figure 9:
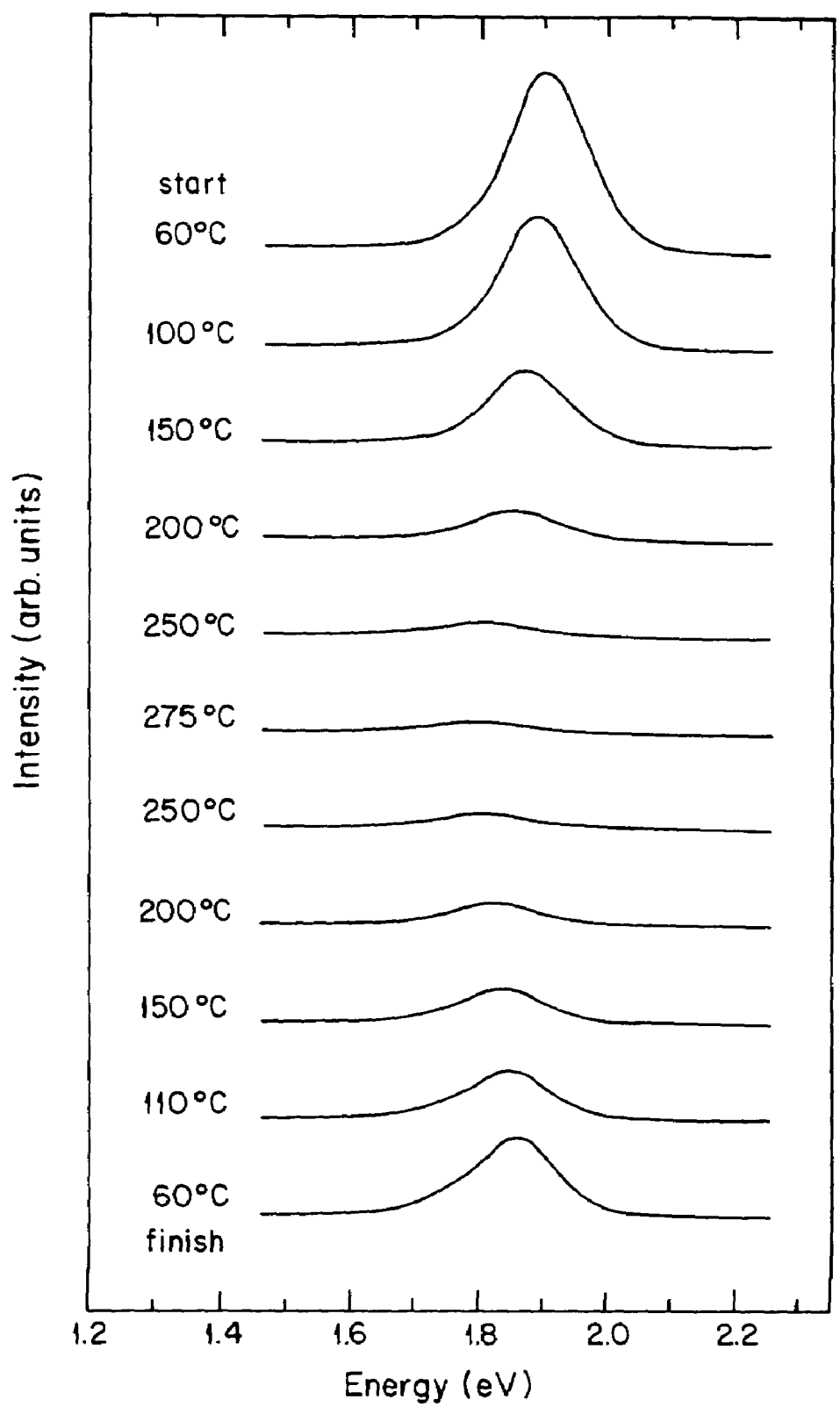
FIG. 9 is a graph depicting the evolution of the photoluminescence as a function of temperature.

The PL of the CdTe nanocrystallites is temperature dependant. A reaction apparatus containing already synthesized 50 Å diameter CdTe nanocrystal growth solution was assembled in the fluorometer sample chamber and attached to a nitrogen source. The temperature of the system was equilibrated for ten minutes and then a spectrum was obtained. FIG. 9 displays the PL spectrum of the nanocrystallites at a range of temperatures. The hysteresis in FIG. 9 is believed to be due to growth and/or decomposition that occurred during the latter half of the experiment.

Transmission electron microscopy (TEM) provides valuable information about the size, shape, and distribution of the CdTe nanocrystal samples. Collecting a large population of measurements ensured statistically meaningful data. A JEOL 2000FX transmission electron microscope operating at 200 kV was used to obtain high resolution images of the CdTe nanocrystallites. 400 mesh copper grids with an ultralight coating of amorphous carbon (Ladd) served as substrates. Solutions of CdTe nanocrystallites were prepared by size selecting once with acetonitrile, washing the powder once with methanol, dissolving in THF, and diluting until the absorbance at the first state was between 0.3–0.6 in a 1 cm cuvette. One drop of this solution was placed onto a carbon grid and, after 10 seconds had elapsed, the excess solution was wicked away with a tissue. An objective aperture was used to improve contrast while still being able to image the (111) lattice spacing, the most intense ring in the diffraction pattern. Measurements were performed on images taken between 210,000–410,000× magnification. Microscope magnification readings were calibrated using the d-spacing of the (111) planes measured by X-ray diffraction (3.742 Å). The instrumental magnification reading was found to be systematically low in this range; all measurements given herein are multiplied by 1.15 to reflect accurate values.

Figure 10:
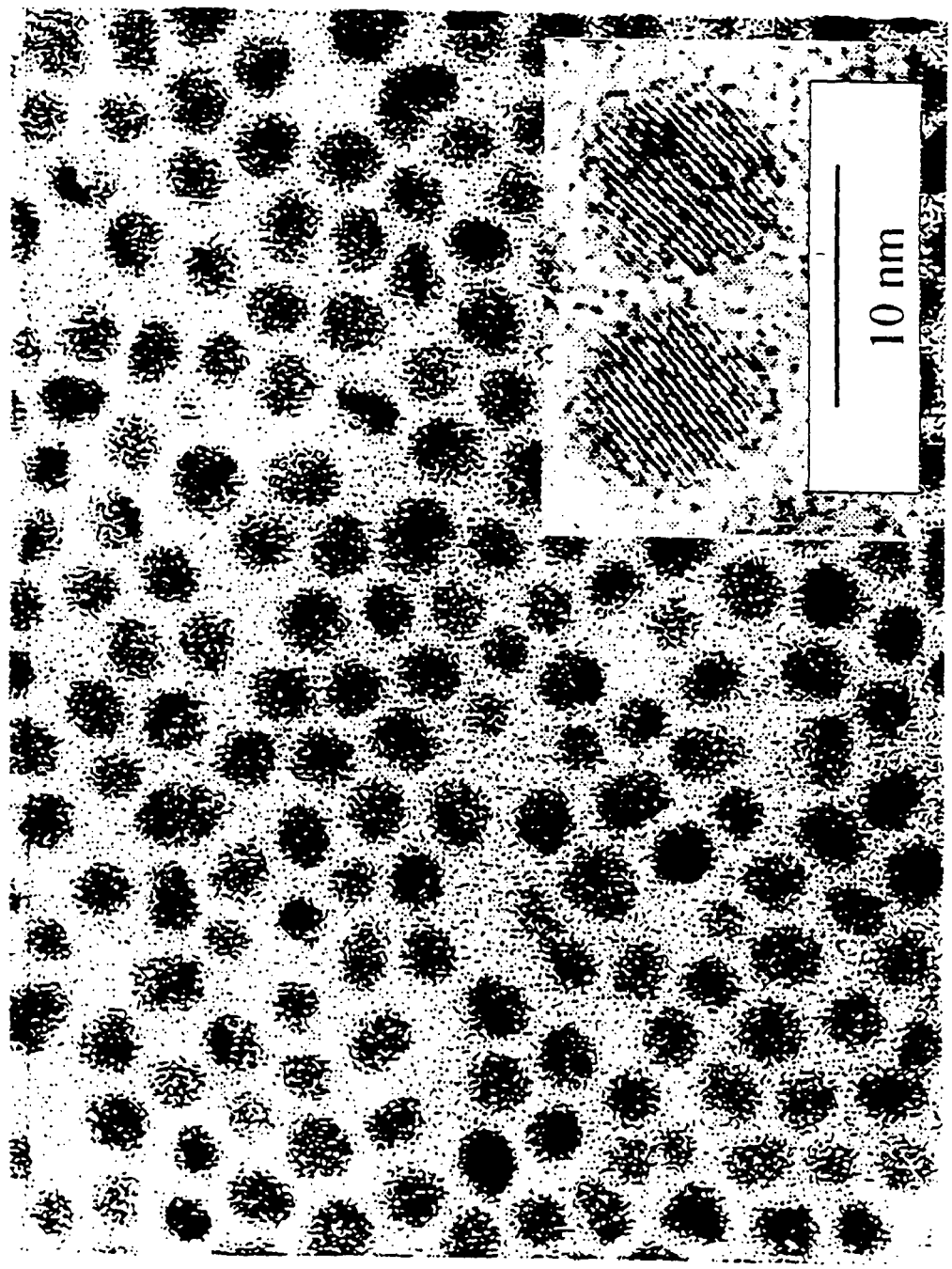
FIG. 10 is a TEM image of telluride semiconductor nanocrystallites.
Figure 11A:
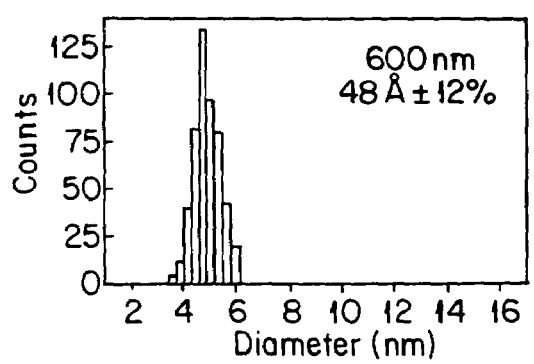
FIG. 11 is a series of graphs depicting size histograms for several nanocrystallite syntheses.
Figure 11B:
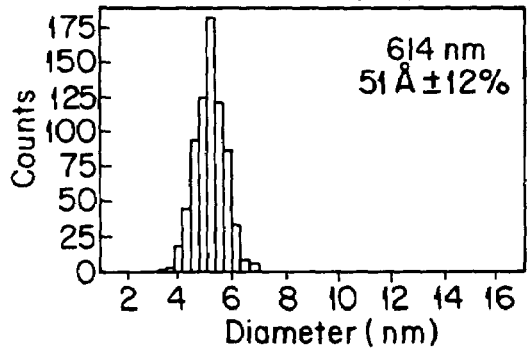
Figure 11C:
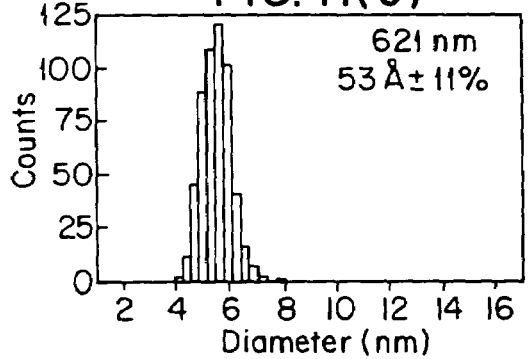
Figure 11D:
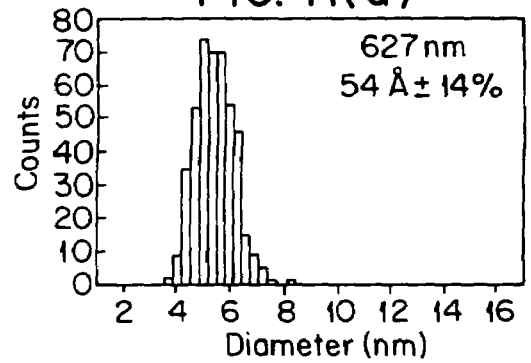
Figure 11E:
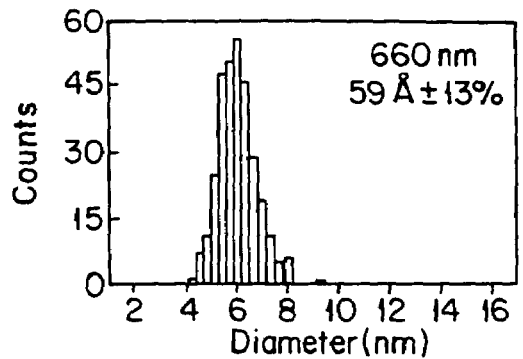
Figure 11F:
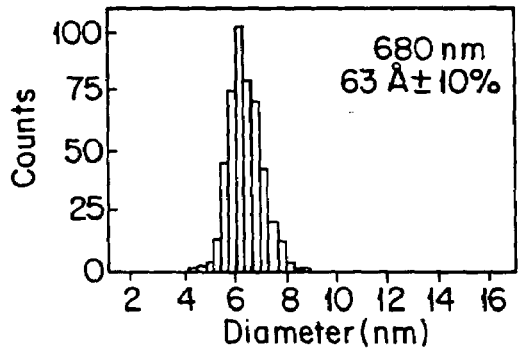
Figure 11G:
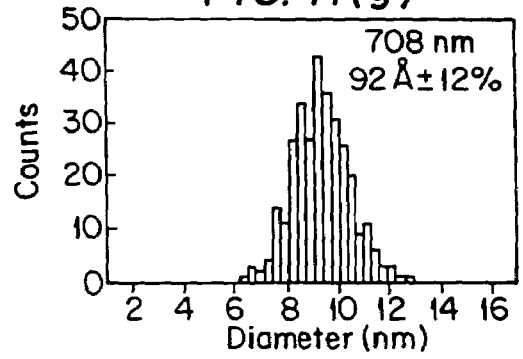
Figure 11H:
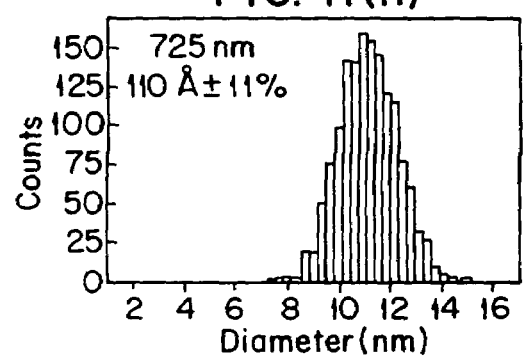

CdTe samples were carefully size selected once with acetonitrile as described in U.S. application Ser. No. 08/969, 302, incorporated herein by reference. The powder was washed once with methanol and then dissolved in THF. Solution concentration was adjusted to deposit a submonolayer coverage of nanocrystallites on the carbon substrate. TEM samples prepared from THF contain few regions of closely aggregated particles and are superior to those laid out from hexane or pyridine. FIG. 10 shows a bright field TEM image of CdTe nanocrystallites from a sample with an average size of 110±12 Å. This figure is representative of the entire sample. Most of the nanocrystallites were approximately the same size and the same spherical shape. However, there was a size distribution, and some nanocrystallites had a distinctly prolate shape. As in the case of CdSe, the population of prolate nanocrystallites was found to increase with size. The inset of FIG. 10 shows neighboring nanocrystallites which were oriented so that the lattice fringes representing (111) planes are visible.

Figure 12:
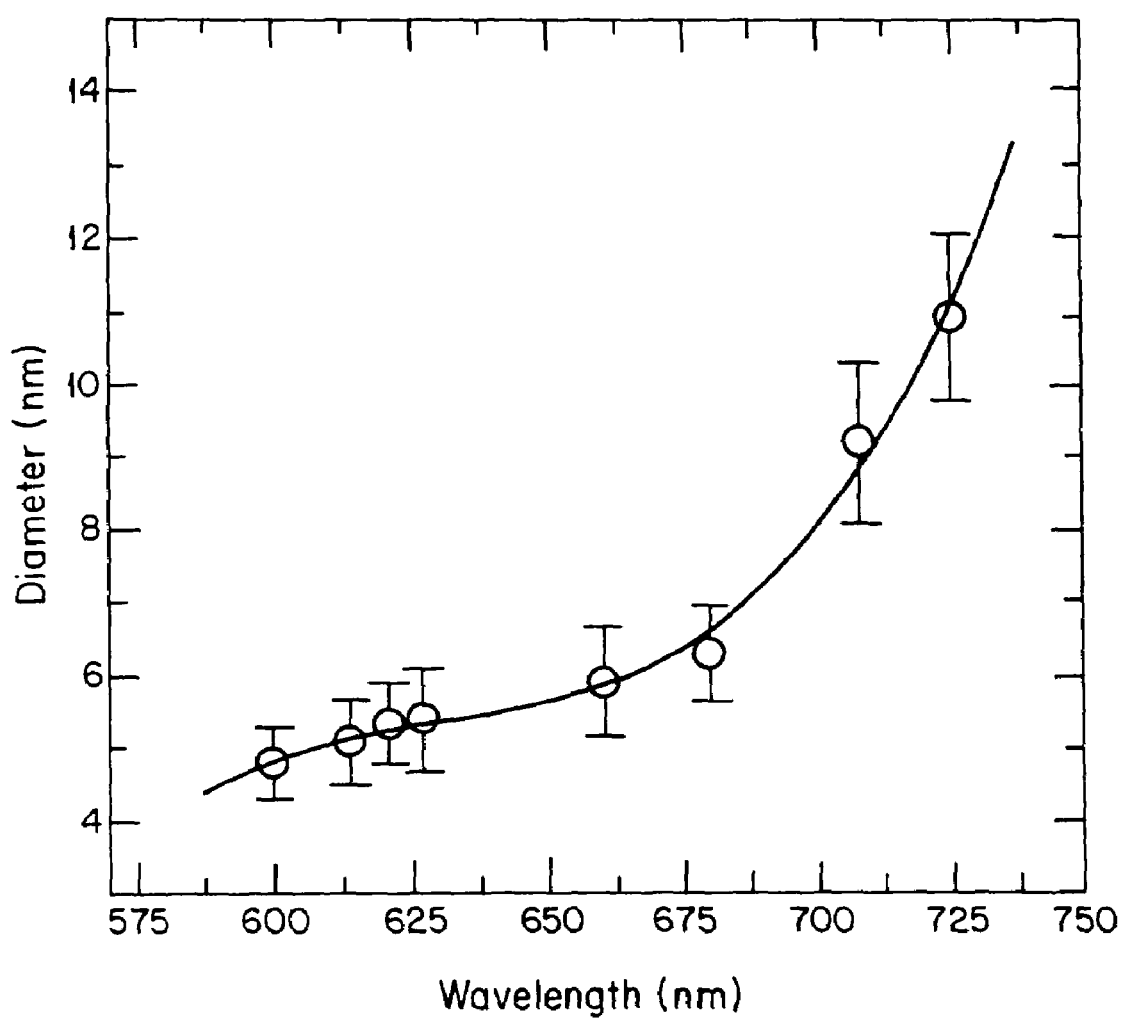
FIG. 12 is a graph depicting the dependence of the photoluminescence on diameter for CdTe nanocrystallites.

For each examined CdTe size at least 250 nanocrystallites—in most cases approximately 500—were measured in order to determine the average diameter. FIG. 11 shows the histograms obtained for 8 different sizes. The standard deviations (10–14%) of nanocrystallites prepared by these methods are large in comparison to the best CdSe samples (<5%). FIG. 12 plots the relationship between diameter and wavelength of the first absorbing state. The line graphs the third order polynomial which best fits the data.

Powder X-ray diffraction (XRD) patterns provided the most complete information regarding the type and quality of the CdTe crystal structure. The random orientation of nanocrystallites in a powder sample ensured that all possible crystal directions were probed. Estimates of size were also possible since particle diameter is inversely related, via the X-ray coherence length, to the peak width.

A Rigaku 300 Rotaflex diffractometer with a Cu anode operating at 60 kV with a 300 milliamp flux was used to obtain powder XRD patterns. Samples were prepared by size selecting CdTe once with acetonitrile, washing the powder three times with methanol, dissolving in the minimum amount of THF to produce a very concentrated solution, casting that solution onto a silicon (001) substrate, and allowing the solvent to evaporate. Powders which would not dissolve in THF were dried under vacuum and stuck onto silicon substrates using RTV silicon adhesive.

Figure 13:
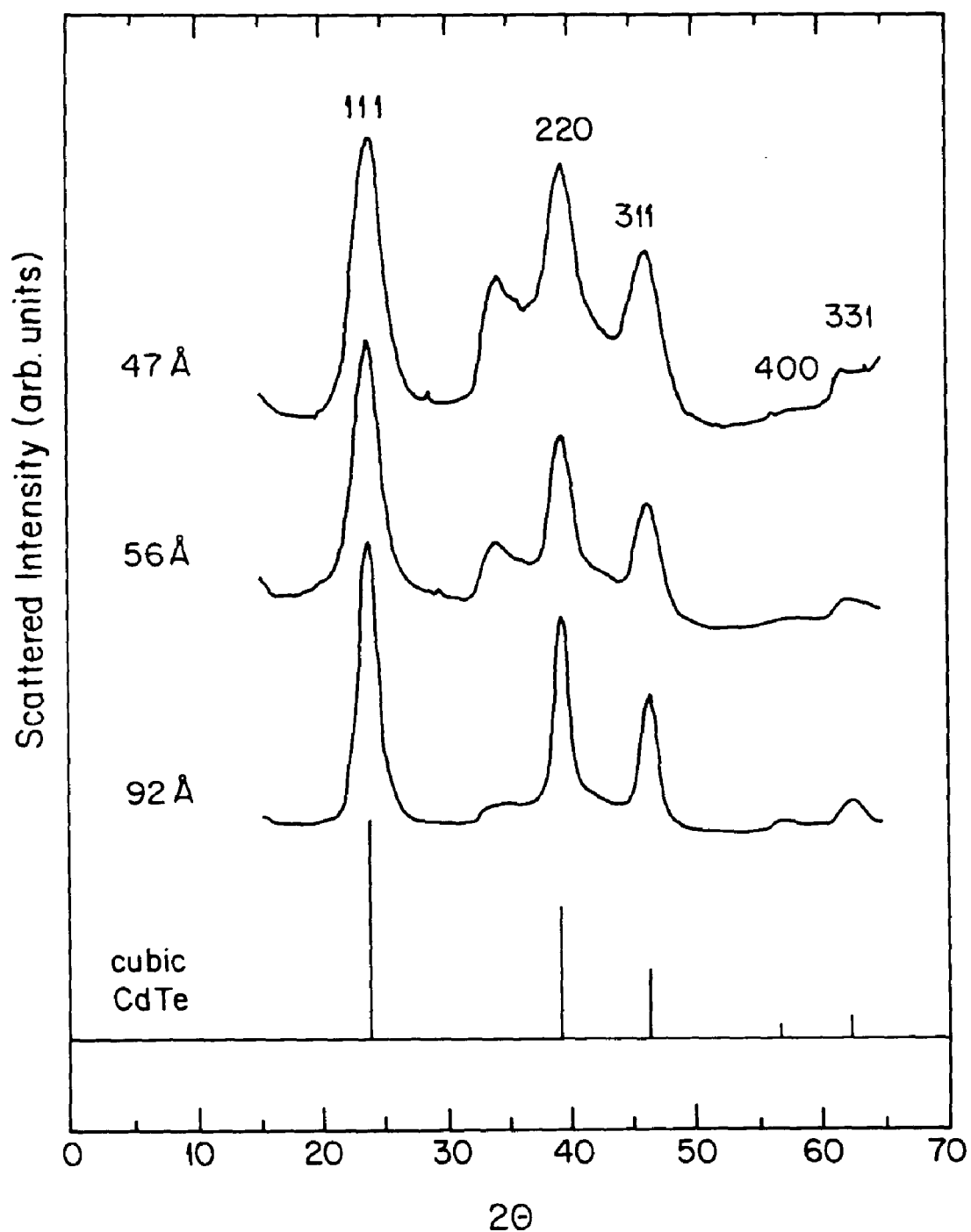
FIG. 13 is a graph depicting x-ray diffraction spectra for three sizes of CdTe nanocrystallites.

FIG. 13 shows the experimental XRD patterns of three different size CdTe samples produced using HPPTTe. The peak positions match those of bulk cubic CdTe, which is represented by the stick spectrum at the bottom of FIG. 13. Cubic CdTe is the thermodynamically stable bulk phase achieved because of high temperature nucleation and growth. Previous lower temperature syntheses produced the less stable wurtzite phase of CdTe. The unassigned peak at 34° is believed to be due to a stacking fault which enhances the equivalent of the (103) direction in the wurtzite structure.

Particle diameters were estimated using the Scherrer equation:

$$L = \frac{0.888 \, (\lambda)}{\Delta(2\Theta)\cos(\Theta)}$$

where L is the coherence length (also known as the Scherrer length) of the X-rays, $\lambda$ is the wavelength of the X-rays, $\Delta(2\Theta)$ is the FWHM in radians, and $\Theta$ is the angle of incidence. The coherence length L is a mathematical construction that is related to real dimensions through the volume average of the particle. For a sphere of diameter D the relationship works out to $$D = \left(\frac{4}{3}\right) L$$

Using these equations and the FWHM of the (111) reflections gives sizes (45, 54, 81 Å) which are only slightly smaller than those obtained by TEM (47, 56, 92 Å). Since the Scherrer method actually measures the coherence length of the X-rays, any crystal imperfections will cause the calculated size to be smaller than the true size. The fact that the XRD sizes are close to the TEM size implies that the samples were very crystalline, at least in the <111> directions.

Overcoating CdTe Nanocrystallites

Figure 14:
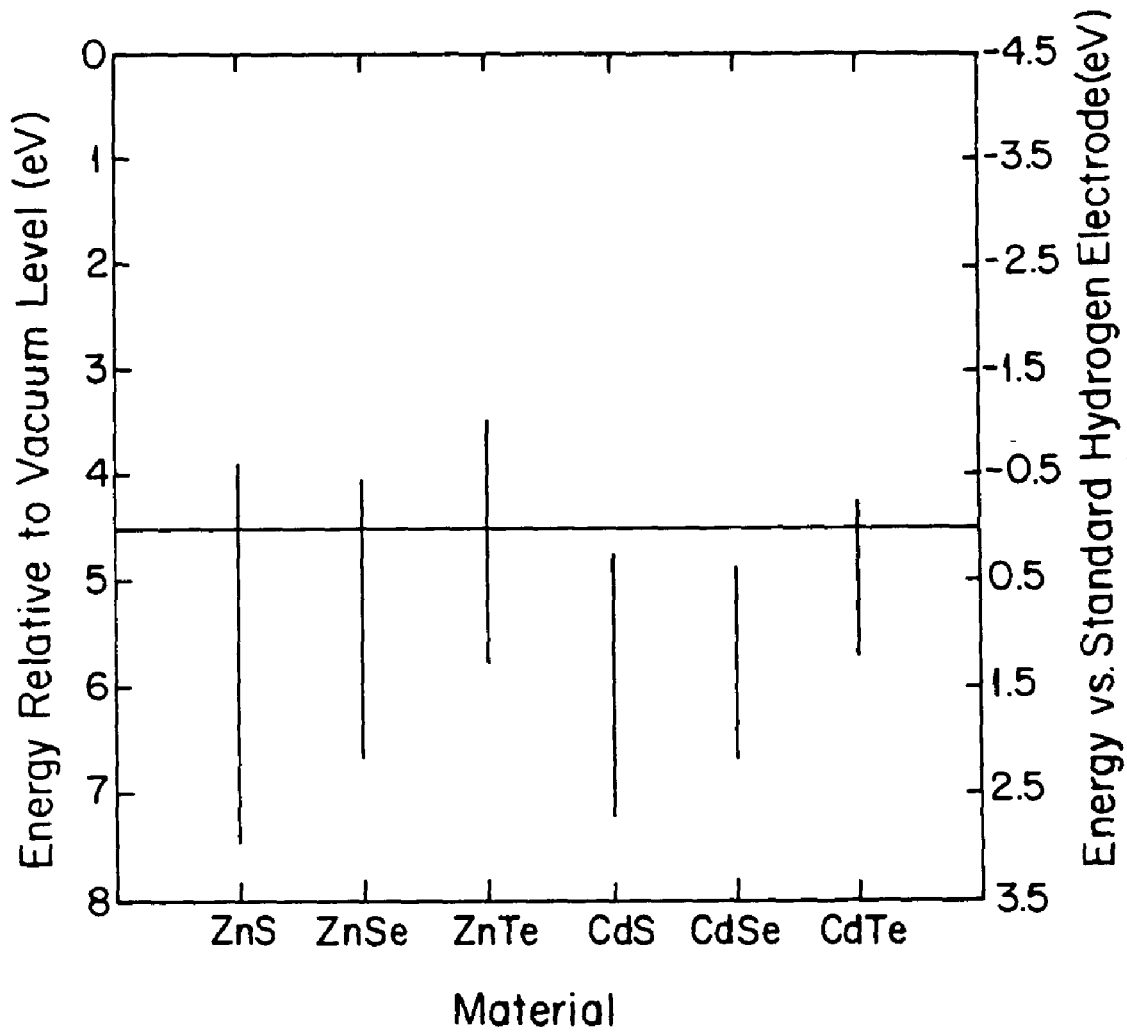
FIG. 14 is a graph depicting the band gaps of several bulk II-VI semiconductors.

While high quantum efficiency from non-overcoated or "bare" CdTe nanocrystallites is very important in and of itself, it also affects the outcome of subsequent protective shell growth attempts. Empirical observations from (CdSe)ZnS and (CdSe)CdS studies show that this overcoating process generally has a multiplicative effect on the quantum efficiency of the starting material: the brightest (core)shell samples generally come from the brightest nanocrystal cores. Semiconductor band offsets must be compared to determine which potential shell materials provide energy barriers for both the electron and hole. Since reliable values have not been published for nanocrystallites, bulk values can be used as a general guide. FIG. 14 shows the positions of the bands relative to the vacuum level for the II-VI zinc and cadmium semiconductors. ZnS and ZnSe appear to be suitable shell material candidates. Growth of ZnS or ZnSe shells onto a CdTe core produces a composite material which is much more robust during processing and manipulation. (CdTe)ZnS and (CdTe)ZnSe overcoated nanocrystallites have been synthesized using both a one-step and a two-step synthesis process.

One-Step Synthesis of Overcoated Nanocrystallites

CdTe nanocrystallites were synthesized as described above. Once the cores had reached the desired size, the temperature was lowered to 200° C. The amounts of Zn and S precursors needed to grow a ZnS shell of desired thickness for each CdTe sample were determined as follows. First, the average radius of the CdTe nanocrystallites was estimated from TEM or SAXS measurements. Next, the ratio of ZnS to CdTe necessary to form a shell of desired thickness was calculated based on the ratio of the shell volume to that of the core volume, assuming a spherical core and shell and using the bulk lattice parameters of CdTe and ZnS. Equimolar amounts of diethyl zinc ($ZnEt_2$) and hexamethyldisilathiane (($TMS)_2S$) were added to 5–10 mL trioctylphosphine (TOP). The Zn and S precursor solution was added dropwise to the stirring CdTe reaction mixture over a period of 5–10 minutes. After the addition was complete the mixture was cooled to 90° C. and left stirring for several hours. 10 mL butanol were added to the mixture to prevent the TOPO from solidifying upon cooling to room temperature. The overcoated particles were stored in their growth solution to ensure that the surface of the nanocrystallites remained passivated with TOPO. (CdTe)ZnSe was synthesized in the same fashion, with bis(trimethylsilyl) selenide (($TMS)_2Se$) serving as the selenium source. For both ZnS and ZnSe overcoats, the quantum efficiency of the PL was increased by 0–20%.

Two-Step Synthesis of Overcoated Nanocrystallites

CdTe nanocrystallites were synthesized as described above. The amount of nanocrystallites was determined by weight and/or optical absorbance. 20 g TOPO was dried under vacuum (0.5 Torr) for 1 hour, then cooled to 60° C. under nitrogen. The CdTe nanocrystallites were dispersed in hexane or THF, mixed with the TOPO, and the solvent subsequently removed under vacuum. The amounts of Zn and S precursors needed to grow a ZnS shell of desired thickness were determined as follows. First, the average radius of the CdTe nanocrystallites was estimated from TEM or SAXS measurements. Next, the ratio of ZnS to CdTe necessary to form the shell was calculated based on the ratio of the shell volume to that of the core volume, assuming a spherical core and shell and using the bulk lattice parameters of CdTe and ZnS. Equimolar amounts of diethyl zinc ($ZnEt_2$) and hexamethyldisilathiane (($TMS)_2S$) were added to 5–10 mL trioctylphosphine (TOP). The Zn and S precursor solution was added dropwise to the stirring CdTe reaction mixture over a period of 5–10 minutes. After the addition was complete the mixture was cooled to 90° C. and left stirring for several hours. 10 mL butanol was added to the mixture to prevent the TOPO from solidifying upon cooling to room temperature. The overcoated particles were stored in their growth solution to ensure that the surface of the nanocrystallites remained passivated with TOPO. (CdTe)ZnSe was synthesized in the same fashion, with bis(trimethylsilyl) selenide (($TMS)_2Se$) serving as the selenium source. For both ZnS and ZnSe overcoats, the quantum efficiency of the PL was increased by 0–20%.

Alternative Size Selection Procedure for CdTe Nanocrystallites

A second size selective precipitation method allows narrower size distributions to be obtained. For example, size distributions of less than 10% RMS deviation can be prepared. CdTe nanocrystals are isolated in air by a modified size selective precipitation. After synthesis of CdTe nanocrystals described elsewhere, the flask is cooled to ~60° C. and mixed with 10 mL of trioctylamine and 10 mL of tetrahydrofuran (THF). Methanol or acetonitrile is added to the mixed solution until the mixture becomes turbid. Size selected CdTe nanocrystals can be obtained as a precipitated powder after centrifugation. Size selected CdTe nanocrystals are moderately soluble to hexanes and extremely soluble to THF. Trioctylamine is added to maintain high quantum efficiency of PL during the size selection procedure as well as to suppress phase separations. It should be used immediately before the size selection procedure to avoid etching of the nanocrystal surface. After size selection, typical FWHM of PL spectrum is 35 nm. Spectra with FWHM as low as 20 nm can be obtained.

Photoluminescence of CdTe Nanocrystals

Figure 15:
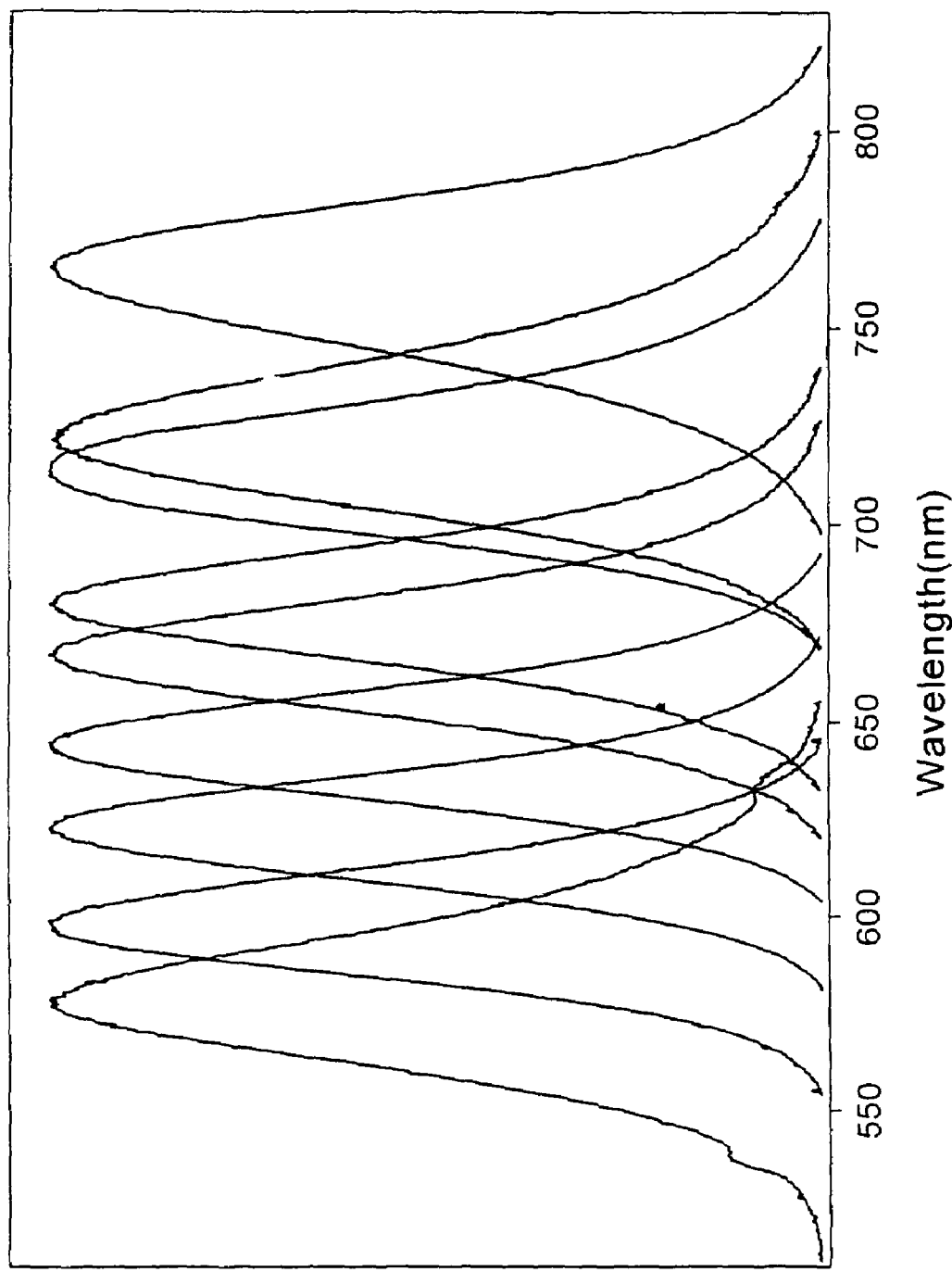
FIG. 15 is a graph depicting the emission spectra of a series of sizes of CdTe nanocrystallites.

FIG. 15 shows the typical room temperature photoluminescence (PL) spectra of CdTe nanocrystallites, which span the optical spectrum ranging from 580 nm to 770 nm. The PL quantum efficiency of these samples range from 40% to 65% with CdTe nanocrystallites emitting around 640 nm having the highest quantum efficiency. The quantum efficiency becomes lower as the size of CdTe nanocrystallites gets smaller or larger from the medium size. Full width half maximum (FWHM) of each spectrum falls in the range of 45 nm to 70 nm before the size selection procedure. After size selection, the FWHM of each emission spectrum drops to 35 nm. The spectra shown in FIG. 15 were obtained using CdTe nanocrystallites having diameters of 4.0 nm, 4.5 nm, 4.8 nm, 5.2 nm, 5.8 nm, 6.2 nm, 7.7 nm, 9.1 nm, 11.9 nm.

A number of embodiments of the invention have been described. Nevertheless, it will be understood that various modifications may be made without departing from the spirit and scope of the invention. For example, the methods and products described herein primarily related to CdTe nanocrystallites. However, it will be apparent to those skilled in the art that these methods and products can be extended to form ZnTe, MgTe, HgTe, and alloys of all of these tellurides. Accordingly, other embodiments are within the scope of the following claims.

What is claimed is:

1. A method of manufacturing nanocrystallites, comprising injecting into a coordinating solvent an M-containing compound, M being selected from the group consisting of Cd, Zn, Mg, and Hg, and a Te-containing compound of the form

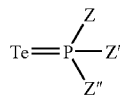

wherein one of Z, Z', and Z" comprises an amide, to form a mixture; and heating the mixture to grow the nanocrystallites.

2. The method according to claim 1, wherein the Te-containing compound has a boiling point of at least 200° C. at atmospheric pressure.

3. The method according to claim 1, wherein each of Z, Z', and Z" is an amide.

4. The method according to claim 1, wherein each of Z, Z', and Z", independently, is —N(A)(A'), wherein each of A and A', independently, is alkyl, alkenyl, aryl, cycloalkyl, or cycloalkenyl.

5. The method according to claim 1, wherein each amide, independently, is a dialkyl amide.

6. The method according to claim 1, further comprising mixing the Te-containing compound and the M-containing compound prior to injecting.

7. The method according to claim 1, further comprising adding additional M-containing compound, additional Te-containing compound, or a mixture thereof, during heating.

8. The method according to claim 1, wherein the Te-containing compound and the M-containing compound are injected sequentially.

9. The method according to claim 1, wherein the Te-containing compound and the M-containing compound are injected substantially simultaneously.

10. The method according to claim 1, further comprising growing an overcoating of a semiconductor on a surface of the nanocrystallite.

11. The method according to claim 1, further comprising separating a size of nanocrystallite by size selective precipitation.

12. The method according to claim 11, wherein an amine is added to the nanocrystallites during size selective precipitation.

13. The method according to claim 1, wherein the nanocrystallite photoluminesces with a full-width at half maximum (FWHM) of 70 nm or less.

14. The method according to claim 1, wherein the FWHM is 45 nm or less.

* * * * *